United States Patent
O'Grady et al.

(10) Patent No.: US 11,505,793 B2
(45) Date of Patent: Nov. 22, 2022

(54) METHOD FOR NUCLEIC ACID DEPLETION

(71) Applicant: UEA Enterprises Limited, Norwich (GB)

(72) Inventors: Justin Joseph O'Grady, Norwich (GB); John Richard Wain, Norwich (GB); Solomon Mwaigwisya, Norwich (GB); Gemma Louise Kay, Norwich (GB)

(73) Assignee: UEA ENTERPRISES LIMITED, Norwich (GB)

( * ) Notice: Subject to any disclaimer, the term of this patent is extended or adjusted under 35 U.S.C. 154(b) by 222 days.

(21) Appl. No.: 16/468,922

(22) PCT Filed: Dec. 12, 2017

(86) PCT No.: PCT/GB2017/053715
§ 371 (c)(1),
(2) Date: Jun. 12, 2019

(87) PCT Pub. No.: WO2018/109454
PCT Pub. Date: Jun. 21, 2018

(65) Prior Publication Data
US 2019/0316113 A1    Oct. 17, 2019

(30) Foreign Application Priority Data
Dec. 14, 2016 (GB) .................................... 1621271

(51) Int. Cl.
*C12Q 1/68* (2018.01)
*C12N 15/10* (2006.01)
(Continued)

(52) U.S. Cl.
CPC ....... *C12N 15/1003* (2013.01); *C12Q 1/6806* (2013.01); *C12Q 1/686* (2013.01); *C12Y 301/04003* (2013.01)

(58) Field of Classification Search
CPC ....................................................... C12Q 1/68
(Continued)

(56) References Cited

U.S. PATENT DOCUMENTS

| | | |
|---|---|---|
| 2005/0014128 A1 | 1/2005 | Ewert et al. |
| 2008/0160528 A1 | 7/2008 | Lorenz |
| 2012/0329081 A1* | 12/2012 | Bennion ............. C12Q 1/66 435/8 |

FOREIGN PATENT DOCUMENTS

| | | |
|---|---|---|
| EP | 2333105 A1 | 6/2011 |
| WO | 2010004265 A1 | 1/2010 |

(Continued)

OTHER PUBLICATIONS

Flores-Diaz et al, Effects of Clostridium perfringens phospholipase C in mammalian cells, Anaerobe. Apr. 2004;10(2):115-23. doi: 10.1016/j.anaerobe.2003.11.002.*

(Continued)

*Primary Examiner* — Aaron A Priest
(74) *Attorney, Agent, or Firm* — Cantor Colburn LLP

(57) ABSTRACT

Provided is a method for depleting host nucleic acid in a biological sample, said sample having been previously obtained from an animal host, said method comprising the steps of (a) adding a cytolysin, or an active variant thereof, to said sample; and (b) carrying-out a process to physically deplete nucleic acid released from host cells within said sample or otherwise render such nucleic acid unidentifiable.

15 Claims, 16 Drawing Sheets
Specification includes a Sequence Listing.

(51) Int. Cl.
  *C12Q 1/6806*    (2018.01)
  *C12Q 1/686*    (2018.01)
(58) Field of Classification Search
  USPC .............................................................. 435/6
  See application file for complete search history.

(56)        References Cited

FOREIGN PATENT DOCUMENTS

WO      2016169579      10/2016
WO    WO-2016169579 A1 *  10/2016    ............... C12N 9/22

OTHER PUBLICATIONS

Sani et al., Bacteria May Cope Differently from Similar Membrane Damage Caused by the Australian Tree Frog Antimicrobial Peptide Maculatin 1.1, J Biol Chem. Aug. 7, 2015;290(32):19853-62. doi: 10.1074/jbc.M115.643262. Epub Jun. 22, 2015.*
Istivan & Coloe, Phospholipase A in Gram-negative bacteria and its role in pathogenesis, Microbiology (Reading). May 2006;152(Pt 5):1263-1274. doi: 10.1099/mic.0.28609-0.*
Schmiel & Miller, Bacterial phospholipases and pathogenesis, Microbes Infect. Nov. 1999;1(13):1103-12. doi: 10.1016/s1286-4579(99)00205-1.*
International Search Report and Written Opinion; International Application No. PCT/GB2017/053715; International Filing Date Dec. 12, 2017; dated Feb. 7, 2019; 15 pages.
Chakraborty et al.; "Molecular Analysis of Bacterial Cytolsin"; Reviews of Infectious Diseases; 9(5); pp. S456-S466; (1987).
Dal Peraro, Matteo et al.; "Pore-forming Toxins: Ancient, but Never Really Out of Fashion"; Nature Reviews / Microbiology; 14; pp. 77-92; (2016).
Feehery et al.; "A Method for Selectively Enriching Microbial DNA from Contaminating Vertebrate Host DNA"; PLoS ONE; 8(10); e76096; 14 pages; (2013).
GB1621271.4 Search Report dated Feb. 3, 2017; 8 pages.
Hasan et al.; "Depletion of Human DNA in Spiked Clinical Specimens for Improvement of Sensitivity of Pathogen Detection by Next-Generation Sequencing"; Journal of Clinical Microbiology; 54(4); pp. 919-927; (2016).
MolYsis(TM); Small, Medium and Large Volumes Removal of Human DNA; 4 pages; https://www.molzym.com/images/products/Flyer_App_Notes/flyer_MolYsis_web.pdf; (2019).
Mwaigwisya et al.; "Emerging Commercial Molecular Tests for the Diagnosis of Bloodstream Infection"; Expert Rev. Mol. Diagn.; 15(5); pp. 681-692; (2015).
Schmidt et al.; "Identification of Bacterial Pathogens and Antimicrobial Resistance Directly From Clinical Urines by Nanopore-based Metagenomic Sequencing"; J Antimicrob Chemother; 72; pp. 104-114; (2017).
Tso et al.; "Cloning and Expression of the Phospholipase C Gene from Clostridium Perfringens and Clostridium Bifermentans"; Infection and Immunity; pp. 468-476; (1989).
Uppalapati et al.; "In Silico, In Vitro and in Vivo Analysis of Binding Affinity Between N and C-Domains of Clostridium Perfringens Alpha Toxin"; PLoS ONE; 8(12); 682024; 10 pages; (2013).
Welch, R.A., "Pore-forming Cytolysins of Gram-negative Bacteria"; Molecular Microbiology; 5(3); pp. 521-528; (1991).

* cited by examiner

METHOD FOR NUCLEIC ACID DEPLETION

CROSS REFERENCE TO RELATED APPLICATIONS

This application is a National Stage application of PCT/GB2017/053715, filed Dec. 12, 2017, which claims the benefit of Application No. GB 1621271.4, filed Dec. 14, 2016, both of which are incorporated by reference in their entirety herein.

FIELD OF THE INVENTION

The invention relates to methods of depleting host nucleic acid from a biological sample.

BACKGROUND TO THE INVENTION

Rapid and comprehensive infectious disease diagnostics are crucial for improved patient management and in the fight against antimicrobial resistance. Rapid diagnosis of life-threatening infectious diseases such as sepsis and pneumonia is paramount. These clinical syndromes have complex aetiologies and require pathogen recognition in challenging sample matrixes e.g. blood, sputum etc. Currently, the "gold standard" method for clinical diagnostics is microbial culture, which is labour intensive, has long turnaround times and poor clinical sensitivity. Currently available rapid molecular methods (e.g. PCR) improve turnaround time to result and sensitivity, but are limited by range and therefore rare pathogens and resistance markers can be problematic. The most applicable technology for rapid detection of microbial pathogens is nucleic acid amplification tests (NAATs). NAATs are available for sepsis diagnostics (e.g. Septifast®, Roche) but complexity of use and suboptimal performance have prevented their widespread adoption. Most of the NAATs for respiratory tract infections (RTIs) focus on the detection of respiratory viruses (e.g. Biofire Filmarray Respiratory Panel, Seegene RV15). An exception is the Curetis Unyvero® test which is designed for health care associated pneumonia. NAATs, however, are not comprehensive (e.g. the Curetis test only covers 90% of the top pathogens), seeking only a pre-set range of targets, meaning that less common pathogens will be missed. Consequently, NAAT diagnostics are an adjunct to standard bacteriology, not a replacement, and adoption is limited.

A paradigm shift in diagnostics technology is urgently required—a universal diagnostic method which can detect any pathogen (e.g. viral, bacterial, fungal) and antibiotic resistance. Agnostic/shotgun metagenomic sequencing has the potential to be the technology of choice to drive this shift. Shotgun metagenomic sequencing can detect and provide relative proportions of viruses, bacteria and fungi in a sample without any prior knowledge of the microbial community present, and is increasingly being used to investigate complex metagenomes in clinical samples.

So why is shotgun metagenomics not currently being widely applied to infection diagnosis? One reason is that next generation sequencing (NGS) has traditionally been expensive, complex to perform and difficult to analyse. The development of MinION® nanopore sequencing technology has changed the NGS landscape with cheap portable sequencers, rapid simple library preparation (15 mins) and automated real-time analysis tools. Another major barrier is the large amount of human DNA present in clinical samples, which is often several orders of magnitude greater than the pathogen DNA present. Blood is a particularly challenging matrix for NGS-based pathogen characterization due to the vast amount of human vs. pathogen nucleic acid (particularly DNA) present (ratio is typically $10^8$:1 to $10^9$:1, based upon $10^6$ leukocytes/ml [with ~6.6 pg DNA/cell] but as few as 1-10 colony forming units [CFU] of pathogen/ml [with ~10 fg DNA/cell]). A host DNA depletion of at least about $10^5$, potentially resulting in a human:pathogen DNA ratio of $10^3$:1, is required to facilitate NGS-based pathogen characterization, a level of depletion (giving rise to pathogen nucleic acid enrichment) not achieved by methods disclosed in the art, such as commercially available pathogen DNA enrichment methods (Looxster® Enrichment kit (Analytic Jena); NEBNext® Microbiome DNA Enrichment kit (NEB); MolYsis® Basic 5 kit (Molzym)).

It is among the objects of this disclosure to address the aforementioned problems.

SUMMARY OF THE INVENTION

Accordingly, provided is a method for depleting host nucleic acid in a biological sample, said sample having been previously obtained from an animal host, said method comprising the steps of:

(a) adding a cytolysin, or an active variant thereof, to said sample; and (b) carrying-out a process to physically deplete nucleic acid released from host cells within said sample or otherwise render such nucleic acid unidentifiable.

Preferably, step (b) comprises adding a nuclease to said sample and/or the method further comprises the step of extracting remaining nucleic acid from the sample.

Preferably, the method further comprises the step of subjecting the extracted nucleic acid to a purification process and/or further comprises the step of amplifying the extracted nucleic acid.

Preferably, the method further comprises the step of conducting a nucleic acid amplification test on the extracted nucleic acid or, preferably, conducting a sequencing process on the extracted nucleic acid.

In preferred embodiments, the cytolysin is a phospholipase, preferably a phospholipase C (PLC), more preferably is a bacterial PLC, more preferably a Group 1 PLC, most preferably PLC from *Clostridium perfringens*.

In preferred embodiments the biological sample is a blood sample.

In preferred embodiments the method results in at least a 10 fold, preferably at least a $10^2$ fold, preferably at least a $10^3$ fold, preferably at least a $10^4$ fold, most preferably at least a $10^5$ fold depletion of host DNA originally contained within the sample.

Also provided is a kit comprising i) a cytolysin, or an active variant thereof, and ii) means to physically deplete free nucleic acid within a biological sample or otherwise render such nucleic acid unidentifiable. Preferably, said cytolysin is as defined as above and/or wherein said means comprises a nuclease.

DETAILED DESCRIPTION OF THE INVENTION

General

Figure 1:
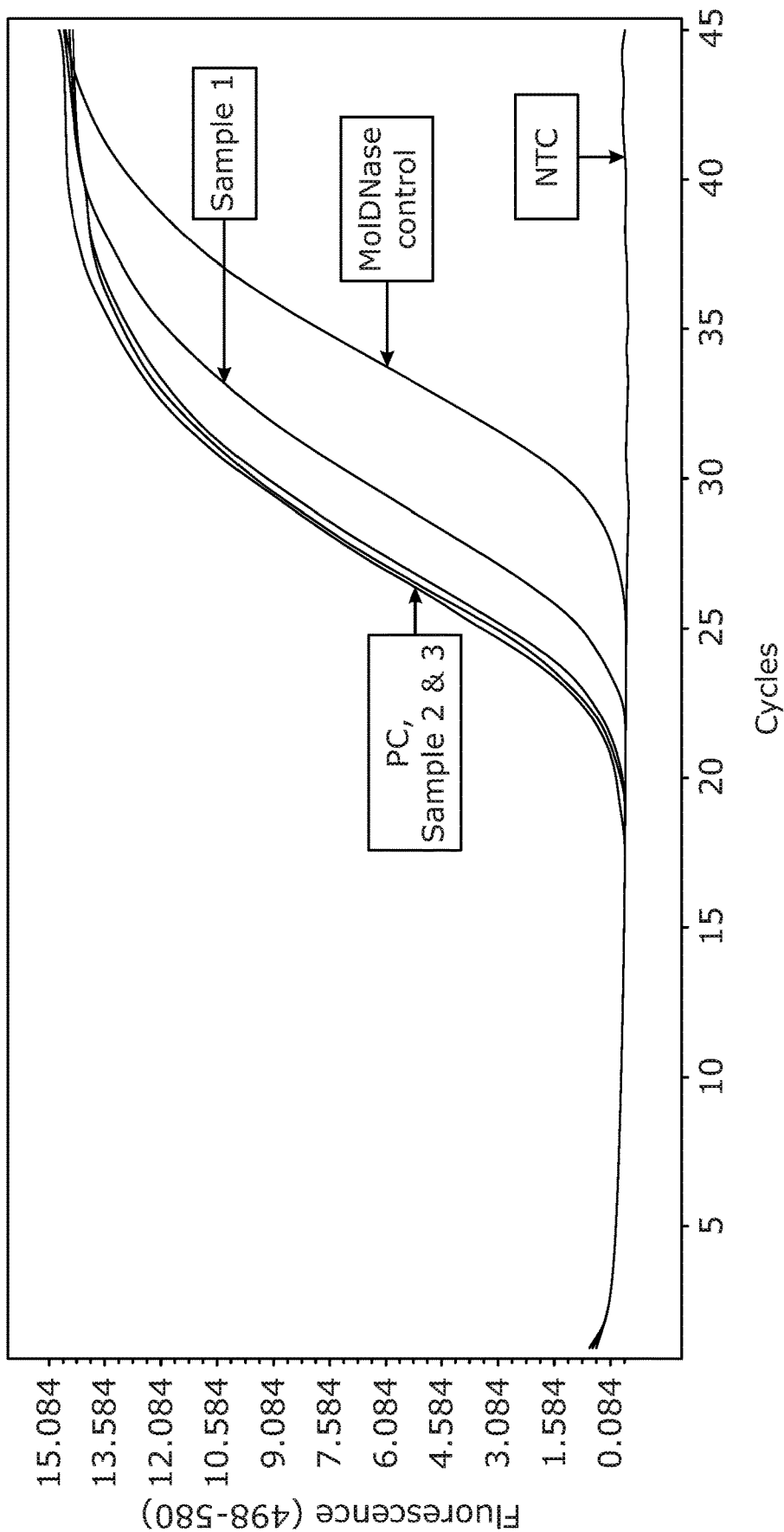
FIG. 1 shows amplification curves of human qPCR results after various endonuclease treatments.

Provided herein is a method for depleting host nucleic acid (particularly RNA and/or, most preferably, DNA) in a biological sample, said sample having been previously obtained from an animal host, said method comprising the steps of:
 (a) adding a cytolysin, or an active variant thereof, to said sample; and
 (b) carrying-out a process to physically deplete nucleic acid released from host cells within said sample or otherwise render such nucleic acid unidentifiable.

The animal host can be a vertebrate, e.g. a bird, a fish or, preferably, a mammal, most preferably a human. The host may, at the time of sample collection, be alive or dead.

The biological sample can be any sample that comprises animal cells (in tissue form or otherwise). Particular (e.g. clinical) samples of interest include bile, nail, nasal/bronchial lavage, bone marrow, stem cells derived from the body, bones, non-fetal products of conception, brain, breast milk, organs, pericardial fluid, buffy coat layer, platelets, cerebrospinal fluid, pleural fluid, cystic fluid, primary cell cultures, pus, saliva, skin, fetal tissue, fluid from cystic lesions, stomach contents, hair, teeth, tumour tissue, umbilical cord blood, mucus and stem cells. Particularly preferred samples include, though, joint aspirates, faeces, urine, sputum and, especially, blood (including plasma). Preferably, the sample is in liquid form. An initial sample might need to be converted to liquid form before conducting the present methodology. A liquid sample might have a volume of between 10 µl and 100 ml, preferably between 10 µl and 50 ml, such as between 10 µl or 100 µl and 20 ml (e.g. 0.2 ml or 1 ml).

The cytolysin causes (selective) lysis of the host cells, releasing host nucleic acid such that it can be (partially or completely) depleted. Nucleic acid within a non host cell or particle (e.g. pathogen) is essentially left intact (i.e. has not been significantly removed from the sample or digested) and identifiable, such that it can be subsequently collected and analysed and, in particular, identified (by e.g. sequencing or targeted PCR). A nucleic acid is identifiable e.g. if its sequence and/or biological origin can be ascertained. Preferably, therefore, the cytolysin is added to the sample and allowed to act for a period of time such that sufficient host cell lysis can occur. Steps (a) and (b) ("cytolysin incubation" and "depletion step") can occur simultaneously, or step (b) follows step (a).

The method of depleting host nucleic acid comprises both physical depletion and (in the context of the present technology) virtual depletion (of nucleic acid released from host cells within the sample). Physical depletion can involve e.g. digesting the nucleic acid (i.e. breaking down nucleic acid polymers to e.g. base monomers) or removing nucleic acid from the sample (e.g. by any nucleic acid capture method known to the skilled person, such as deploying nucleic acid-binding magnetic beads in the sample to bind DNA and/or RNA, which can subsequently be removed or harvested from the sample).

Virtual depletion involves rendering (released) nucleic acid unidentifiable (via, in particular, targeted PCR or, most preferably, sequencing). For DNA, this means rendering the DNA non-amplifiable (e.g. by PCR) and/or (preferably) non-sequenceable. For RNA, this means rendering the RNA non-amplifiable, non-reverse-transcribable and/or (preferably) non-sequenceable. A preferred process for such rendering (particularly for DNA) involves adding a photoreactive nucleic acid-binding dye, such as propidium monoazide (PMA) or ethidium monoazide (EMA), to the sample and inducing photoreaction.

Most preferably, however, the method of depletion is via digestion of nucleic acid, most preferably via enzymatic digestion. It is therefore preferred that step (b) comprises adding a nuclease to the sample. Preferably, the nuclease is added to the sample and allowed to act for a period of time such that sufficient nucleic acid digestion can occur. Preferably, therefore, a deoxyribonuclease (DNase) and/or a ribonuclease (RNase) is added to the sample (and preferably allowed to act for a period of time such that sufficient DNA/RNA digestion can occur). The nuclease can have both DNase and RNase activity (e.g. HL-SAN DNase). Depletion of host DNA is important if analysis of non host (e.g. pathogen) DNA is to be carried out. Depletion of host RNA is important if analysis of non host (e.g. pathogen) RNA is to be carried out, and indeed can facilitate the optimisation of DNA analysis (e.g. DNA sequencing).

In such embodiments, the method preferably further comprises the subsequent step of neutralising the (or each) nuclease (i.e. decreasing or substantially eliminating the activity of the nuclease). The skilled person will recognise a range of neutralisation options, to be selected for each depletion protocol. This might include heat inactivation or, preferably, buffer exchange (i.e. the removal of a buffer in which the nuclease is active and/or replacement with or addition of a buffer in which the nuclease is substantially inactive). Preferably, the temperature of the sample (at any/all stage(s) at/before extraction of remaining nucleic acid from the sample) is maintained at 50° C. or less, preferably 45° C. or less, preferably 40° C. or less, to optimise subsequent release of nucleic acid from the pathogen (particularly from bacterial cells).

Further Steps

In preferred embodiments, the method further comprises the step of extracting remaining (preferably non host) nucleic acid from the sample (or aliquot thereof). Part or all of the remaining nucleic acid (particularly non host nucleic acid) will be intact and identifiable.

Typically, the extraction process will involve a centrifugation step to collect, in particular, non host cells/particles (e.g. pathogens) (virus particles and/or, in particular, bacterial and/or non-animal (e.g. non-mammalian) (e.g. unicellular) eukaryotic cells, such as fungi), from which the nucleic acid can be obtained. Centrifugation conditions can be selected such that bacterial and non-animal cells, but not virus particles, are pelleted, or such that virus particles are pelleted in addition to bacterial and non-animal cells. If the former, standard virus detection tests could be performed on the supernatant. (Indeed, prior to any addition of cytolysin, one might centrifuge a clinical sample, keep the cell-containing pellet (for the method of the current technology), and keep the supernatant for virus detection using standard procedures, with or without enrichment using the present technology.)

Nucleic acid can be obtained from the pathogen(s) using methods known in the art, and might involve the addition of a lysis buffer, a lytic enzyme(s) (degrading or abrogating cell membranes, cell walls and/or viral capsids), and/or a protease, e.g. proteinase K. Preferred lytic enzymes include lysozyme, mutanolysin, lysostaphin, chitinase and lyticase.

Optionally, the extracted nucleic acid (or aliquot thereof) is subject to a purification process, such as one known in the art. During purification of DNA, RNase is optionally used to facilitate the optimisation of subsequent DNA sequencing. However, RNase is omitted from any purification step if non host (e.g. pathogen) RNA extraction is of interest (for e.g. subsequent RNA sequencing) (and a DNase might be used to assist with purification).

In preferred embodiments, extracted nucleic acid (or aliquot thereof) is subject to an amplification process, such as whole genome amplification, to increase the copy number of the nucleic acid, particularly where the biological sample is a blood sample. For RNA, this might involve direct amplification or conversion of RNA to cDNA, followed by amplification of cDNA.

In preferred embodiments, the method further comprises the step of conducting a nucleic acid amplification test (e.g. targeted PCR amplification process, isothermal amplification, nucleic acid sequence-based amplification (NASBA)) on the extracted nucleic acid (RNA, DNA or cDNA) (or aliquot thereof) or, preferably, conducting a sequencing process on the extracted nucleic acid (or aliquot thereof), such as (e.g. short or long read) DNA or RNA sequencing, using e.g. nanopore or Illumina® sequencing.

In the preceding embodiments, nucleic acid (particularly host nucleic acid) previously rendered unidentifiable will not be amplified by any amplification process and/or (in particular) sequenced by any sequencing process.

The new method, in comparison with methods of the prior art (e.g. the MolYsis® technique, which deploys chaotropic agents to lyse host cells prior to host nucleic acid digestion), facilitates highly improved depletion of host nucleic acid (particularly DNA), while leaving non host (e.g. pathogen, particularly bacterial) nucleic acid intact (and identifiable), leading to highly improved non host (e.g. pathogen) nucleic acid enrichment, sufficient for subsequent sequencing-based (e.g. next-generation sequencing [NGS] based) (e.g. pathogen) diagnostics. A key factor in this advance has been the ability to achieve e.g. a $5 \times 10^4$ or greater, such as $10^5$ or greater (e.g. $10^6$ or greater), fold depletion of host DNA from within biological sample from a mammalian host, and these are preferable outcome features of the present technology (as is a fold depletion of 10 or greater, $10^2$ or greater, $10^3$ or greater, $5 \times 10^3$ or greater, or $10^4$ or greater). It is particularly preferred that host nucleic acid (e.g. DNA) is undetectable (e.g. via qPCR) following deployment of the method of the invention. In more general terms, the selective depletion of host nucleic acid enables enrichment of non host nucleic acid, and hence improved identification of non host organisms. This technology is thus applicable to fields other than medical microbiology, such as biological research, veterinary medicine/diagnostic, and agriculture/food safety The Cytolysin A cytolysin (also known as a cytolytic toxin) is a protein secreted by a microorganism, plant, fungus or animal which is specifically toxic to a heterologous cell type(s), particularly promoting lysis of target cells. Preferred cytolysins are those secreted by microorganisms, particularly by bacteria, and/or those that are toxic to an animal (e.g. mammalian) cell type(s).

The cytolysin can be a cytolysin that has a detergent effect on the target cell membrane (e.g. a 26 amino acid delta toxin produced by *Staphylococcus*) or forms pores in the target cell membrane (e.g. Alpha hemolysin from *S. aureus*, Streptolysin O from *S. pyogenes*, and Perfringiolysin 0 produced by *C. perfringens*). See e.g.:

Alpha hemolysin from *S. aureus*—https://www.ncbi.nlm.nih.gov/proteinBBA23710.1 (SEQ ID No. 2):

```
  1 mktrivssvt ttlllgcilm npvanaadsd iniktgttdi gsnttvktgd lvtydkengm
 61 hkkvfysfid dknhnkkilv irtkgtiagq yrvyseegan ksglawpsaf kvqlqlpdne
121 vaqisdyypr nsidtkeyms tltygfngnv tgddsgkigg liganvsigh tlkyvqpdfk
181 tilesptdkk vgwkvifnnm vnqnwgpydr dswnpvygnq lfmktrngsm kaadnfldpn
241 kassllssgf spdfatvitm drkaskqqtn idviyervrd dyqlywtstn wkgtntkdkw
301 tdrsseryki dwekeemtn
```

Streptolysin O from *S. pyogenes*—https://www.ncbi.nlm.nih.gov/proteinBAD77794.2 (SEQ ID No. 3):

```
  1 msnkktfkky srvaglltaa liignlvtan aesnkqntas tettttseqp kpesseltie
 61 kagqkmddml nsndmiklap kemplesaek eekksedkkk seedhteein dkiyslnyne
121 levlaknget ienfvpkegv kkadkfivie rkkkninttp vdisiidsvt drtypaalql
181 ankgftenkp davvtkrnpq kihidlpgmg dkatvevndp tyanvstaid nlvnqwhdny
241 sggntlpart qytesmvysk sqieaalnvn skildgtlgi dfksiskgek kvmiaaykqi
```

-continued

```
301 fytvsanlpn npadvfdksv tfkdlqrkgv sneapplfvs nvaygrtvfv kletssksnd 361 veaafsaalk gtdvktngky sdilenssft avvlggdaae hnkvvtkdfd virnvikdna 421 tfsrknpayp isytsvflkn nkiagvnnrt eyvettstey tsgkinlshq gayvaqyeil 481 wdeinyddkg kevitkrrwd nnwysktspf stviplgans rnirimarec tglawewwrk 541 viderdvkls keinvnisgs tlspygsity k
```

Preferably, the cytolysin is a cytolysin that digests a cell membrane component, (e.g. phospholipids, i.e. is a phospholipase). An example is Sphingomylinease (also know as beta-toxin) from *S. aureus*, see e.g. https://www.ncbi.nlm.nih.gov/protein/CAA43885.1 (SEQ ID No. 4):

```
  1 mmvkktksns lkkvatlala nlllvgaltd nsakaeskkd dtdlklvshn vymlstvlyp 61 nwgqykradl igqssyiknn dvvifneafd ngasdkllsn vkkeypyqtp vlgrsqsgwd 121 ktegsysstv aedggvaivs kypikekiqh vkcsgegfdn dsnkgfvytk iekngknvhv 181 igthtqseds rcgaghdrki raeqmkeisd fvkkknipkd etvyiggdln vnkgtpefkd 241 mlknlnyndv lyaghnstwd pqsnsiakyn ypngkpehld yiftdkdhkq pkqlvnevvt 301 ekpkpwdvya fpyyyvyndf sdhypikays k
```

The phospholipase can be a phospholipase A, B, C or D, such as PLD from *Streptomyces*, see e.g. https://www.ncbi.nlm.nih.gov/protein/BAL15170.1 (*Streptomyces vinaceus*) (SEQ ID No. 5):

```
  1 mhrhtpslrr psahlpsala vraavpaall alfaavpasa apaagsgadp aphldaveqt 61 lrqvspgleg qvwertagnv ldastpggad wllqtpgcwg ddkctarpgt eqllskmtqn 121 isqatrtvdi stlapfpnga fqdaivsglk tsaargnklk vrvlvgaapv yhlnvlpsky 181 rdelvaklga darnvdlnva smttsktafs wnhskllvvd gqsvitggin dwkddyleta 241 hpvadvdlal rgpaaasagr yldelswstc qnksniasvw fassngaacm pamakdtapa 301 apapapgdvp avavgglgvg ikrndpsssf rpalpsapdt kcvvglhdnt nadrdydtvn 361 peesalrtli ssanrhieis qqdvnatcpp lprydirvyd alaarmaagv kvrivvsdpa 421 nrgavgsggy sqikslseis dtlrdrlalv tgdqgaakat mcsnlqlatf rssqsptwad 481 ghpyaqhhkv vsvddsafyi gsknlypawl qdfgyvvesp aaaaqlnarl lapqwqysra 541 tatidheral cqs
```

Preferably the phospholipase is a phospholipase C (PLC) (i.e. a phospholipase that cleaves before the phosphate, releasing diacylglycerol and a phosphate-containing head group). Preferably the PLC is a bacterial PLC, selected from any of the following groups:

Group 1—Zinc metallophospholipases
Group 2—Sphingomyelinases (e.g. sphingomyelinase C)
Group 3—Phosphatidylinositol
Group 4—Pseudomonad PLC A Group 1 PLC is preferred, particularly PLC from *Clostridium perfringens*, see e.g. https://www.ncbi.nlm.nih.gov/protein/EDT77687.1 (SEQ ID No.1):

```
  1 mkrkickali caalatslwa gastkvyawd gkidgtgtha mivtqgvsil endmsknepe
 61 svrknleilk enmhelqlgs typdydknay dlyqdhfwdp dtdnnfskdn swylaysipd
121 tgesqirkfs alaryewqrg nykqatfylg eamhyfgdid tpyhpanvta vdsaghvkfe
181 tfaeerkeqy kintagcktn edfyadilkn kdfnawskey argfaktgks iyyshasmsh
241 swddwdyaak vtlansqkgt agyiyrflhd vsegndpsvg knvkelvayi stsgekdagt
301 ddymyfgikt kdgktqewem dnpgndfmtg skdtytfklk denlkiddiq nmwirkrkyt
361 afpdaykpen ikviangkvv vdkdinewis gnstynik
```

This cytolysin provides for highly effective lysis of animal host cells in the present technology, despite reports in the literature that purified *C. perfringens* PLC when used alone has no cytotoxic activity against leukocytes.

The cytolysin can be a wild-type cytolysin or an active variant (produced e.g. by recombinant DNA technology). An active variant of a cytolysin is a variant of a cytolysin that retains the ability to lyse a target cell, demonstrating e.g. at least 10%, preferably at least 25%, preferably at least 50%, preferably at least 60%, preferably at least 70%, preferably at least 80%, preferably at least 90%, preferably at least 95% of the activity of the wild-type protein in any assay where lytic activity against a target cell can be shown for the wild-type protein.

"An active variant thereof" includes within its scope a fragment of the wild-type protein. In preferred embodiments, a fragment of the wild-type protein is selected that is at least 10% of the length of the wild-type protein sequence, preferably at least 20%, preferably at least 30%, preferably at least 40%, preferably at least 50%, preferably at least 60%, preferably at least 70%, preferably at least 80%, preferably at least 90% and most preferably at least 95% of the length of the wild-type protein sequence.

"An active variant thereof" also includes within its scope a protein sequence that has homology with the wild-type protein sequence, such as at least 50% identity, preferably at least 60%, preferably at least 70%, preferably at least 80%, preferably at least 85%, preferably at least 90%, preferably at least 95%, preferably at least 97%, and most preferably at least 99% identity, for example over the full wild-type sequence or over a region of contiguous amino acid residues representing 10% of the length of the wild-type protein sequence, preferably at least 20%, preferably at least 30%, preferably at least 40%, preferably at least 50%, preferably at least 60%, preferably at least 70%, preferably at least 80%, preferably at least 90% and most preferably at least 95% of the length of the wild-type protein sequence. Methods of measuring protein homology are well known in the art and it will be understood by those of skill in the art that in the present context, homology is calculated on the basis of amino acid identity (sometimes referred to as "hard homology").

The homologous active cytolysin variant typically differs from the wild-type protein sequence by substitution, insertion or deletion, for example from 1, 2, 3, 4, 5 to 8 or more substitutions, deletions or insertions. The substitutions are preferably 'conservative', that is to say that an amino acid may be substituted with a similar amino acid, whereby similar amino acids share one of the following groups: aromatic residues (F/H/W/Y), non-polar aliphatic residues (G/A/P/I/L/V), polar-uncharged aliphatics (C/S/T/M/N/Q) and polar-charged aliphatics (D/E/K/R). Preferred subgroups comprise: G/A/P; I/L/V; C/S/T/M; N/Q; D/E; and K/R.

The cytolysin or active variant (as described above) may have any number of amino acid residues added to the N-terminus and/or the C-terminus provided that the protein retains lytic activity. Preferably, no more than 300 amino acid residues are added to either or both ends, more preferably no more than 200 amino acid residues, preferably no more than 150 amino acid residues, preferably no more than 100 amino acid residues, preferably no more than 80, 60 or 40 amino acid residues, most preferably no more than 20 or 10 or 5 amino acid residues.

Preferably, the sample is subject to mixing after the cytolysin has been added.

Preferably, to promote cytolysin activity, particular buffering conditions and/or incubation temperature might be provided for any one selected cytolysin. Cytolysin incubation can take place at e.g. between 5° C. and 50° C., such as between 15° C. and 45° C. (e.g. 37° C.), and for between 1 min and 120 min, preferably between 1 min and 60 min, more preferably between 1 min and 30 min (e.g. 15 min or 20 min). For part or all of the cytolysin incubation, the sample is preferably subject to mixing/shaking, at e.g. between 1 and 1500 rpm, preferably between 1 and 1000 rpm (e.g. at 500 rpm or 1000 rpm).

Preferably, the cytolysin is used in the sample at a concentration of at least 0.1 mg/ml, such as between 0.1 mg/ml and 100 mg/ml, preferably between 0.1 mg/ml and 100 mg/ml, preferably between 1 mg/ml and 100 mg/ml (e.g. at 40 mg/ml).

The DNase

If a DNase is used in the present methodology, the DNase can be an endonuclease or an exonuclease (or a combination thereof can be provided), preferably an endonuclease.

Preferred DNases (particularly where the biological sample is a blood sample) include HL-SAN DNase (heat labile salt activated nuclease, supplied by Arcticzymes) and MolDNase (endonuclease active in the presence of chaotropic agents and/or surfactants, supplied by Molzym), and active variants are also contemplated, essentially as discussed above in relation to the cytolysin.

Preferably, the sample is subject to mixing after the DNase has been added. Preferably, to promote DNase activity, particular buffering conditions and/or incubation temperature might be provided for any one selected DNase. DNase incubation can take place at e.g. between 5° C. and 50° C., such as between 15° C. and 45° C. (e.g. 37° C.), and for between 1 min and 120 min, preferably between 1 min and 60 min, more preferably between 1 min and 30 min (e.g. 15 min). In particularly preferred embodiments, the DNase buffer is added to the sample, containing the cytolysin, and incubated (e.g. as described above) before pelleting. The pellet is then resuspended in DNase buffer and the DNase itself is added (ahead of further incubation).

The Biological Sample

Preferably, the biological sample is a blood sample. Preferably, where the sample is blood, the cytolysin targets/lyses (e.g. human) leukocytes.

Preferably, especially where the sample is blood and/or the cytolysin is PLC from *Clostridium perfringens*, the sample comprises a chelating agent (e.g. EDTA).

Kits

Also provided is a kit comprising a cytolysin (according to e.g. any of the aspects described above) (preferably with a buffer for the cytolysin) and means to physically deplete free nucleic acid within a biological sample or otherwise render such nucleic acid unidentifiable. Free nucleic acid includes nucleic acid not contained within a cell or virus particle (e.g. has been released/liberated from animal cells within the sample as a result of lysis of those cells).

The means can be e.g means for nucleic acid capture (using e.g. magnetic bead technology), means for rendering nucleic acid unidentifiable (e.g. PMA or EMA) or, preferably, a nuclease (e.g. a DNase) (preferably with a suitable buffer and/or a composition for inactivating the nuclease), according e.g. to any of the aspects described above.

General

Please note that wherever the term 'comprising' is used herein we also contemplate options wherein the terms 'consisting of' or 'consisting essentially of' are used instead. In addition, please note that the term 'protein' used herein can be used interchangeably with the term 'polypeptide'.

EXAMPLES

In the context of medical microbiology, metagenomics sequencing needs to achieve sufficient genome coverage to identify the pathogenic species present and preferably detect all resistance markers, whether mutational or acquired. To deliver this we estimate that a minimum of 10× genome coverage is required. We directly sequenced (HiSeq) blood, spiked with pathogen cells (*Escherichia coli*), which delivered human reads only, highlighting the need for pathogen DNA enrichment (data not shown). Hence, host DNA depletion is required to reliably and cost effectively apply metagenomics to infectious disease diagnosis.

Here, we describe the process of developing a simple, rapid and highly efficient human DNA depletion method to enable downstream metagenomic sequencing (and other molecular applications e.g. PCR) for the detection and identification of pathogens and associated antibiotic resistance markers.

For efficient and cost effective metagenomic diagnosis of infection, human DNA depletion or pathogen DNA enrichment is essential. We took the human DNA depletion approach focussing on differential lysis of human cells, and removal of human DNA, leaving intact non-human pathogens for further analysis. We used blood as a model sample type, as blood represents one of the most complex clinical samples to successfully apply metagenomic infection diagnosis due to the very high ratio of human:pathogen DNA (as high as $10^9:1$).

We applied cytolysins for differential lysis of human cells and endonucleases (DNases) for digestion of liberated DNA. We tested a number of DNases to determine the most efficient in blood. We then combined the most efficient DNases with various cytolysins to determine whether and how efficiently these toxins would lyse the DNA-containing leukocytes in blood.

A positive control (PC) was added in to every experiment, which was DNA extracted from 200 μl of blood. For cytolysin experiments, the blood was spiked with appropriate pathogen entities, e.g. the most common sepsis causing pathogens (*E. coli* and *S. aureus*), *C. albicans, A. niger*, HBV, or HIV, to ensure that pathogens were not lysed during the procedure. For all qPCR reactions, a no template control (NTC; molecular grade nuclease free dH$_2$O) was included. A MolDNase control sample (from the MolYsis® kit, Molzym, Germany) was also included where appropriate as it has been proven to work in blood.

Subsequently, DNA was extracted as follows (unless otherwise stated in the experimental procedure):

1. Bacterial lysis buffer (to a maximum volume of 380 μl) and proteinase K (20 μl) was added to the treated sample and mixed by vortexing. No bacterial lysis buffer was added to blood samples that were not spiked with bacteria (volume made up to 400 μl with PBS where necessary).
2. All samples were incubated at 65° C. for 5 min
3. Followed by purification on the MagNAPure®

For all experiments, human and non human nucleic acid was quantified using qPCR. Specific hydrolysis probe assays were designed or taken from the literature to detect human, *E. coli* and *S. aureus* DNA (all were single copy gene targets; RNA polymerase II, cyaA and eap respectively). In addition, fungal and viral targets included *C. albicans* 5.8S rRNA, *A. niger* ITS1-2, HBV X gene, and HIV 5' nuclease assay in LTR gene. All qPCR results are presented as amplification curves and/or quantification cycle (Cq) values (this represents the cycle at which the fluorescence signal increases above background which is directly related to the quantity of starting template concentration). The relative concentration of DNA in samples was calculated using the ΔCq (every 3.3 cycles represents a 10-fold difference in concentration; the higher the Cq value the less starting template DNA was present in the sample).

Example 1—Efficacy of Endonucleases for DNA Digestion in Blood

Initial focus was on identifying an endonuclease that would digest DNA released from leukocytes so that the efficacy of cytolysins could be easily assessed in blood. In this experiment, blood samples were freeze thawed three times to release human DNA and an endonuclease; either DS-DNase, HL-SAN DNase (heat labile, salt active nuclease) or micrococcal nuclease from *S.aureus* was added, incubated at 37° C. and DNA was extracted. Controls included a positive control (PC—DNA from 200 μl spiked blood without DNase treatment), a MolDNase control (known to work in blood) and a negative control (NTC—nuclease free water), as detailed above. Human specific qPCR was performed on all DNA extracts and Cq values were compared to determine whether the endonuclease treatment worked.

Detailed Procedure:

1. To lyse blood cells, samples were frozen at −70° C. and thawed at room temperature (RT) three times
2. Freeze-thawed blood was aliquoted into 5×200 μl samples
3. To sample 1, 5 μl of HL-SAN DNase (28.4 U/μl) was added
4. To sample 2, 5 μl of DS-DNase (2 U/μl) was added
5. To sample 3, 20 μl of nuclease micrococcal (resuspended in 100 μl of nuclease free water; 0.62 U/μl) was added
6. All samples were mixed by vortexing
7. Samples 1-3 and PC were incubated at 37° C. for 30 min 8. To the MolDNase control sample, 50 µl of DB1 buffer was added followed by 5 µl of MolDNase then incubated at RT for 15 min
9. All reactions were stopped by adding 5 µl of DNase inactivation buffer (Ambion®, life Technologies®)
10. DNA was extracted and quantified by human qPCR (as described above)

Results:

As shown in Table 1 and FIG. 1, DS-DNase (sample 2) and nuclease micrococcal (sample 3) showed no endonuclease activity on human DNA in blood samples, with ΔCq<1 compared with PC. With a ΔCq of 2.2, HL-SAN DNase (sample 1) showed endonuclease activity resulting in an approximate 4-fold reduction in human DNA when compared to the PC. As previously stated MolDNase was known to work in blood samples and showed the greatest endonuclease activity with the highest Cq value.

TABLE 1

Human qPCR results after various endonuclease treatments

| Sample ID | Endonuclease | Human qPCR (Cq) |
|---|---|---|
| 1 | HL-SAN DNase | 24.77 |
| 2 | DS-DNase | 22.80 |
| 3 | Nuclease micrococcal | 22.35 |
| MolDNase control | MolDNase | 29.47 |
| PC | — | 22.58 |

Conclusion:

From all the endonucleases tested in this experiment, HL-SAN DNase was the only one to show the potential to work effectively in blood. HL-SAN DNase was the endonuclease of choice selected for further testing. As HL-SAN DNase is known to be most active in high salt concentrations, we aimed to test a high salt buffer to improve activity, and Example 2 details buffer optimization.

Example 2—Optimization of HL-SAN Buffer Conditions

From Example 1, HL-SAN DNase was chosen as the most promising endonuclease to work in blood. As HL-SAN DNase is a salt active enzyme, we tested the addition of a high salt buffer to optimize HL-SAN DNase activity on human DNA in blood samples. A high-salt buffer was made and added in various volumes to freeze-thawed blood samples with HL-SAN DNase, incubated at the known working temperature (37° C.), DNase inhibitor was added and samples further incubated. MolDNase control, PC and NTC were included; all samples were subjected to DNA extraction and human qPCR (as detailed above).

HL-SAN buffer components:

10 mM Tris HCl, 100 mM magnesium and 1 M NaCl pH8.5

Detailed Procedure:
1. To lyse blood cells, 2 ml of blood was frozen at −70° C. and thawed at RT three times
2. Freeze-thawed blood was spiked with human DNA and aliquoted into 5× 200 µl samples
3. To sample 1, 20 µl of HL-SAN buffer and 3 µl of HL-SAN DNase was added
4. To sample 2, 100 µl of HL-SAN buffer and 3 µl of HL-SAN DNase was added
5. To sample 3, 180 µl of HL-SAN buffer and 3 µl of HL-SAN DNase was added
6. The above reactions were incubated at 37° C. for 15 min
7. To the MolDNase control, 50 µl of DB1 buffer and 5 µl MolDNase was added and incubated at RT for 15 min
8. All reactions were stopped by adding 5 µl of DNase inactivation buffer (Ambion®, life Technologies®)
9. DNA was extracted and quantified by human qPCR (as described above)

Figure 2:
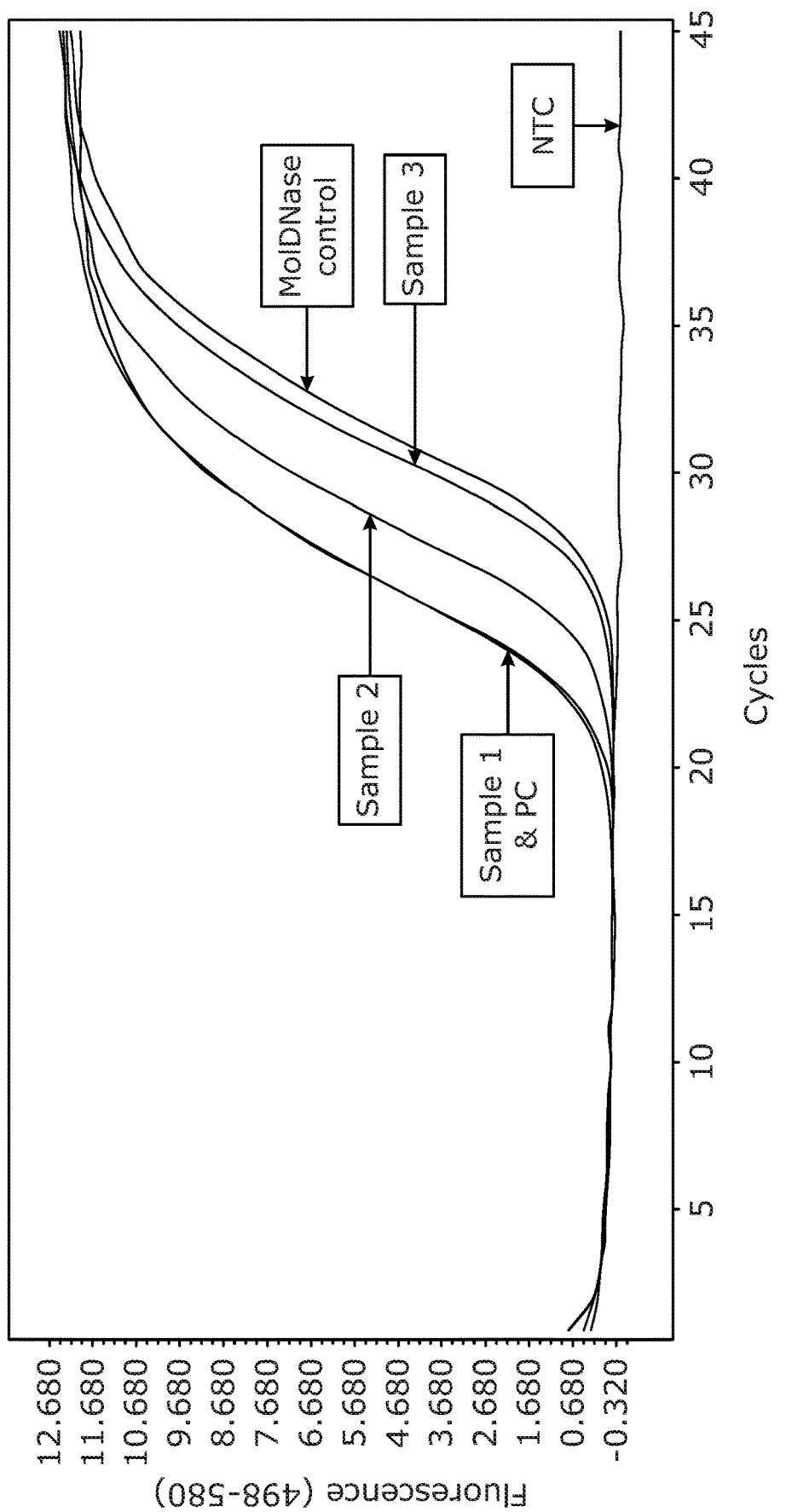
FIG. 2 shows amplification curves of human qPCR results after endonuclease treatment with various buffer volumes.

Results:

Table 2 and FIG. 2 show that the addition of HL-SAN buffer increases the activity of HL-SAN DNase in correlation with an increase in volume. The most effective amount of HL-SAN buffer was 180 µl, which resulted in a similar activity to MolDNase (<1 Cq difference between DNase treatments) and reduced the level of human DNA approximately 32-fold (ΔCq5) compared to no endonuclease treatment (PC). In the absence of buffer, HL-SAN DNase alone, resulted in a human qPCR Cq value of 24.77 (Table 1), with the addition of 180 µl HL-SAN buffer this increased to 27.02Cq (Table 2), showing an increase in HL-SAN DNase activity to reduce human DNA approximately 4-fold (ΔCq 2).

TABLE 2

Human qPCR results after endonuclease treatment with various buffer volumes

| Sample ID | Conditions | Human qPCR (Cq) |
|---|---|---|
| 1 | 20 µl HL-SAN buffer + HL-SAN DNase | 22.27 |
| 2 | 100 µl HL-SAN buffer + HL-SAN DNase | 24.64 |
| 3 | 180 µl HL-SAN buffer + HL-SAN DNase | 27.02 |
| MolDNase control | 50 µl DB1 buffer + MolDNase | 27.63 |
| PC | — | 22.32 |
| NTC | — | — |

Conclusion:

The addition of a high salt buffer (HL-SAN buffer) increased the efficiency of HL-SAN DNase to digest human DNA present in the blood samples after cell lysis by freeze-thawing. Using this combination (HL-SAN buffer and HL-SAN DNase) enabled approximately the same level of human DNA depletion as the known control (MolDNase). Therefore, to test the robustness of the optimized HL-SAN DNase method, the experiment was repeated (with an adjusted volume of HL-SAN buffer required due to limitations of input volume for DNA extraction) against MolDNase with respective DB1 buffer (Example 3).

Example 3—Comparison of HL-SAN DNase and MolDNase Activity

Here, we tested the robustness of the optimized method selected from Example 2 and compared the activity of HL-SAN DNase and MolDNase with their respective buffers. The volume of HL-SAN buffer which provided the same level of activity between HL-SAN DNase and MolDNase was 180 µl, however, due to the volume input limitation of the MagNAPure® for DNA purification, the volume of HL-SAN buffer was reduced to 150 µl. Blood cells were lysed by freeze-thawing, spiked with human DNA and HL-SAN DNase or MolDNase was added with their respective buffer, incubated and followed by enzyme heat inactivation. PC was also included, and DNA was extracted from all samples and human qPCR carried out.

Detailed Procedure:
1. To lyse blood cells, 2 ml of blood was frozen at −70° C. and thawed at RT three times
2. Freeze-thawed blood was spiked with human DNA and aliquoted into 4× 250 µl samples
3. To the HL-SAN DNase sample, 150 µl of HL-SAN buffer (Example 2) and
4 µl of HL-SAN DNase was added, mixed by vortexing and incubated at 37° C. for 15 min
4. To the MolDNase control sample, 50 µl of buffer DB1 and 4 µl of MolDNase was added, mixed by vortexing and incubated at RT for 15 min
5. To the MolDNase control sample and PC PBS was added to increase the sample volume to 400 µl (the required input volume for the MagNAPure®)
6. DNase activity was stopped by heat killing the enzymes at 65° C. for 10 min
7. DNA was extracted and quantified by human qPCR (as described above)

Figure 3:
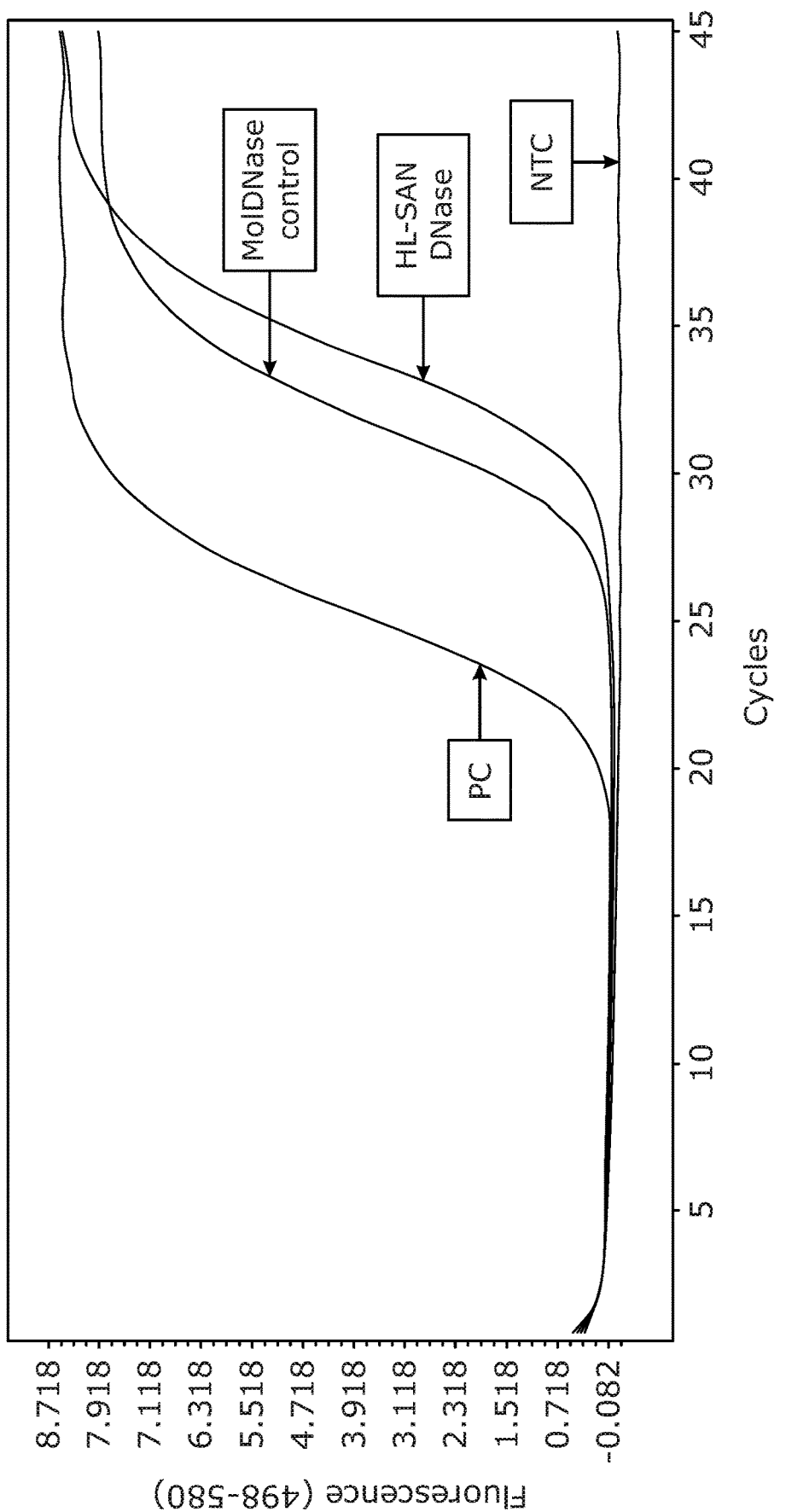
FIG. 3 shows amplification curves of human qPCR results after HL-SAN DNase and MolDNase treatment with respective buffers.
Figure 4:
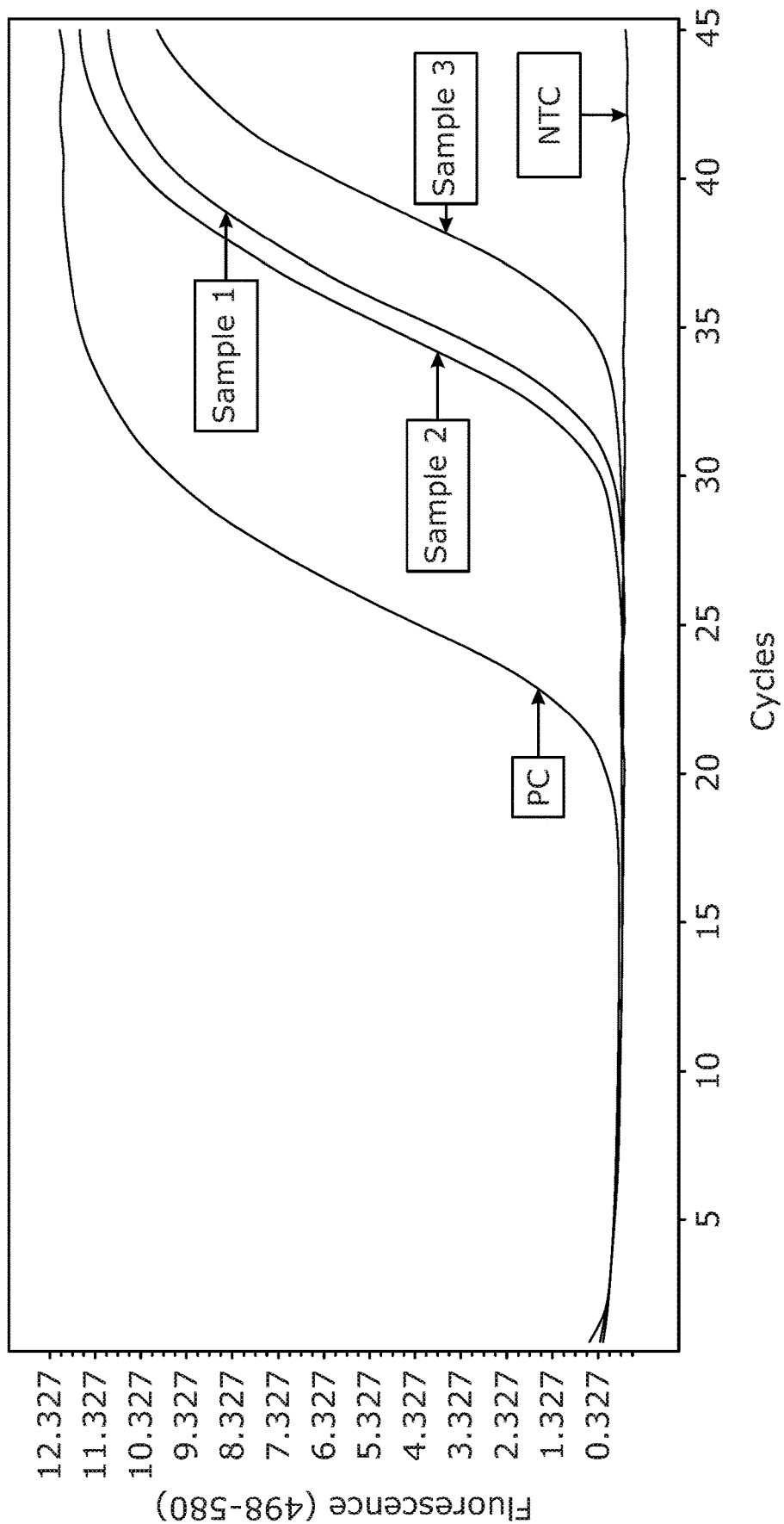
FIG. 4 shows amplification curves of human qPCR results after cytolysin treatment.

Results:

Table 3 and FIG. 3 show that the optimized HL-SAN DNase method out performs the MolDNase control. There is a difference of approximately ΔCq 2 which equates to an approximate 4-fold reduction in human DNA.

TABLE 3

Human qPCR results of HL-SAN DNase and MolDNase treatment with respective buffers

| Sample ID | Human qPCR (Cq) |
|---|---|
| HL-SAN DNase | 30.54 |
| MolDNase control | 28.23 |
| PC | 21.80 |
| NTC | — |

Conclusion:

Under optimized buffer conditions, HL-SAN DNase can work as, if not more, effectively as MolDNase in blood to deplete human DNA. At this point we continued to work with HL-SAN DNase as our endonuclease of choice and began the process of selecting a suitable cytolysin. Example 4 details the different cytolysins that we initially chose to evaluate for leukocyte cell lysis ability/efficacy.

Example 4—Host DNA Depletion Using Streptolysin O and Alpha Hemolysin

After identifying HL-SAN DNase as an effective endonuclease for the digestion of DNA, we investigated the potential of cytolysins to target and lyse specific cell types. Here, we evaluated the activity of two membrane pore forming cytolysins, namely streptolysin O (*Streptococcus pyogenes*) and alpha hemolysin (*Staphylococcus aureus*), on leukocyte lysis. Cytolysins were added (individually and in combination) to blood to lyse host cells. Samples were then incubated and released DNA from lysed cells was digested with MolDNase and a DNase inactivation reagent added after further incubation. PC and NTC samples were included and DNA was extracted from all samples and DNA quantified by human qPCR (as detailed above).

Cytolysin Purchase Information:
Streptolysin O
  Cat number no. S5265-25ku
  Lot number 025M4059V
  25,000-50,000 u/vial
  0.71 mg Solid
  229577 Units/mg solid
  4794117 Units/mg protein
Alpha-Hemolysin
  Cat no H9395-5 MG
  Lot no 095M4057V
  28840 Units/mg Solid
  49647 units/mg protein Detailed Procedure:
1. Streptolysin O and alpha-Hemolysin (0.71 mg (163,000 units) and 5 mg (144,200 units) respectively) was resuspended in 350 µl of nuclease-free water
2. To sample 1, 50 µl of Streptolysin O was added to 200 µl of blood
3. To sample 2, 50 µl of alpha-hemolysin was added to 200 µl of blood
4. To sample 3, 50 µl of Streptolysin O and 50 µl of alpha-hemolysin was added to 200 µl of blood
5. All samples were mixed by vortexing and incubated at 37° C. with shaking at 400 rpm for 30 min
6. After incubation, 150 µl of HL-SAN buffer was added, followed by 3 µl of HL-SAN DNase
7. Samples were further incubated at 37° C. for 15 min
8. DNase activity was stopped by heat killing the enzymes at 65° C. for 10 min
9. To samples 1-3, 100 µl of bacterial lysis buffer was added and to the PC sample 180 µl of bacterial lysis buffer was added
10. DNA was extracted from all samples and human qPCR used to quantify human DNA (as detailed above)

Results:

When used alone streptolysin O and alpha-hemolysin showed approximately the same leukocyte lysis efficacy (Table 3), providing an approximate $10^3$ fold depletion of DNA. Using both cytolysins in combination (alpha-hemolysin and streptolysin O in combination) on the same blood sample, resulted in improved leukocyte lysis efficiency and improved human DNA depletion with an approximate further 10-fold reduction (ΔCq 3.3) in human DNA.

TABLE 4

Human qPCR results after cytolysin treatment

| Sample ID | Cytolysin | Human qPCR (Cq) |
|---|---|---|
| 1 | Streptolysin O | 31.96 |
| 2 | Alpha-hemolysin | 31.32 |
| 3 | Alpha-hemolysin & streptolysin O | 35.31 |
| PC | — | 21.79 |
| NTC | — | — |

Conclusion:

Here we show that membrane pore forming cytolysins are able to target human cells and enable host DNA depletion. Interestingly, it was the combination of the two cytolysins that produced the greatest human DNA depletion. As we had shown that cytolysins could target human cells and demonstrated that host DNA depletion was possible with this approach, we switched our focus to another member of the cytolysins, namely phospholipase C (PLC) from *C. perfrin-*

*gens* (which is a cytolysin that breaks down phospholipids in bilayer membranes of eukaryotic cells) (Example 5).

Example 5—Investigation of PLC Activity on Host Cell Lysis

As previously mentioned, PLC is a cytolysin produced by *C. perfringens* and acts by targeting and breaking down phospholipids in the bilayer membrane of eukaryotic cells. We therefore wanted to test PLC for specific host cell lysis and subsequent host DNA digestion using HL-SAN DNase. PLC is a known zinc metallophospholipase and requires the presence of zinc for activity; it was however unknown whether the concentrations of zinc in human blood would be sufficient for PLC to work. Also required for PLC activity are calcium and magnesium ions. With these experiments using blood collected with EDTA preservative, there was a concern that EDTA would chelate the required calcium and metal ions necessary for PLC activity. Therefore, we tested PLC on blood with no preservative, blood containing EDTA preservative and on blood in the presence of a metal ion containing buffer. PLC was added to the various blood sample types and incubated with shaking for host cell lysis. HL-SAN DNase (with HL-SAN buffer) was then added and incubated for host DNA digestion followed by heat inactivation of HL-SAN DNase. PC and NTC samples were included, and DNA was extracted from all samples followed by human qPCR (as detailed in above).

PLC Buffer Components:
0.1M $ZnCl_2$ and 0.1M $MgCl_2$
Detailed Procedure:
1. PLC (4 mg) was reconstituted in 100 μl of molecular grade water (40 μg/μl)
2. Blood was aliquoted into 4× 250 μl
3. To sample 1 (without EDTA preservative) and sample 2 (with EDTA preservative), 20 μl of PLC was added and mixed well by vortexing, followed by incubation at 37° C. with shaking at 500 rpm for 15 min
4. After incubation, 150 μl of HL-SAN buffer and 4 μl of HL-SAN DNase was added to samples 1 and 2, mixed well by vortexing and incubated at RT for 15 min
5. To sample 3, 150 μl of HL-SAN buffer and PLC buffer was added followed by 4 μl of HL-SAN DNase and 20 μl of PLC then mixed by vortexing and incubated for 15 min at 37° C. without shaking
6. PC was topped up with 150 μl of PBS (total 400 μl)
7. HL-SAN DNase was inactivated by incubating all samples at 65° C. for 10 min
8. DNA was extracted from all samples and human qPCR used to quantify human DNA (as detailed in Section 3)

Figure 5:
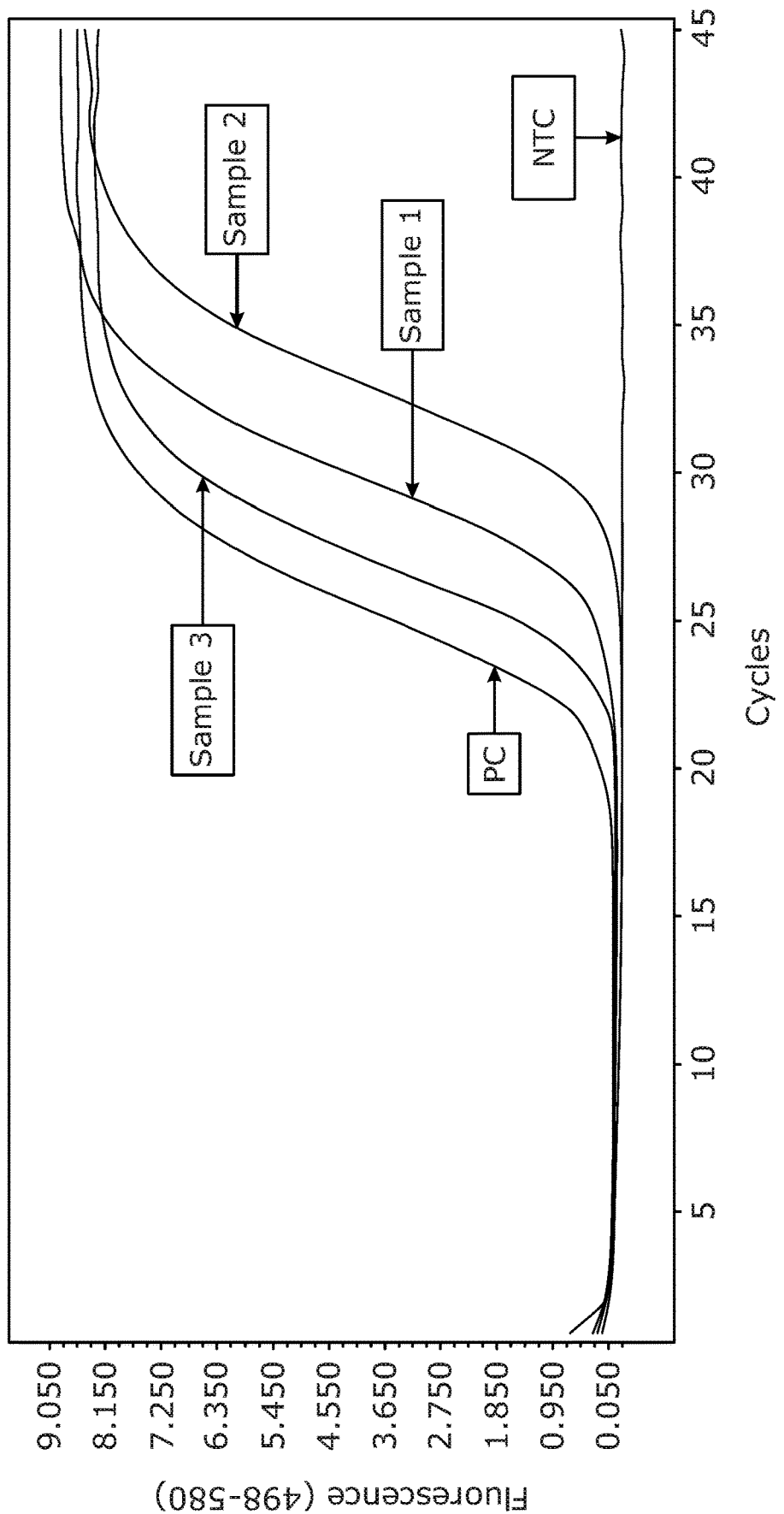
FIG. 5 shows amplification curves of human qPCR results showing PLC activity in different sample conditions.

Results:
There was no improvement in human DNA depletion when PLC was tested on blood with no preservative or with PLC buffer (Table 5 and FIG. 5) in fact, the lack of EDTA or addition of PLC buffer reduced the efficacy of depletion. Sample 2 showed the highest level of host DNA depletion with an approximate 100-fold reduction in human DNA compared to the PC (ΔCq6).

TABLE 5

Human qPCR results of PLC activity in different sample conditions

| Sample ID | Conditions | Human qPCR (Cq) |
|---|---|---|
| 1 | PLC on raw blood | 26.36 |
| 2 | PLC on EDTA blood | 29.45 |
| 3 | PLC combined with PLC buffer | 21.87 |
| PC | — | 23.59 |
| NTC | — | — |

Conclusion:
Despite PLC being known to require calcium, magnesium and zinc ions for activity, the addition of buffer containing these ions appeared to decrease the efficiency of PLC to lyse host cells. After concerns that the preservative EDTA would chelate the metal ions required for PLC activity, we observed that PLC worked better in blood samples preserved with EDTA and was less effective in blood without any preservative. All previous experiments were performed in a volume of 200-250 μl of blood to test the efficiency of PLC and HL-SAN DNase on human DNA depletion. We next wanted to increase the working volume of blood due to the low number of bacterial cells known to be present per millilitre of septic blood (potentially as few as 1 colony forming unit per millilitre) (Example 6).

Example 6—Investigation of PLC Activity on Host DNA Depletion and Bacterial DNA Recovery in an Increased Volume of Blood The pauci-microbial nature of sepsis means that testing larger volumes of blood increases diagnostic sensitivity. Therefore, we wanted to test the activity of PLC in a larger volume of blood (1 ml) and also determine if PLC had any unwanted activity on bacterial cells. Blood was spiked with the most common sepsis causing pathogens (*E. coli* and *S. aureus*). Spiked blood was incubated with PLC to enable host cell lysis, followed by the addition of HL-SAN DNase (with HL-SAN buffer) for DNA digestion and the endonuclease was heat inactivated. A PC sample was included and DNA was extracted from all samples, followed by qPCR for human, *E. coli* and *S. aureus* DNA (as detailed above).

Detailed Procedure:
1. PLC (4 mg) was reconstituted in 100 μl of molecular grade water (40 μg/μl)
2. Blood spiked with *E. coli* and *S. aureus* cultures was aliquoted into 1× 1 ml and 1× 200 μl samples
3. To 1 ml of spiked blood, 100 μl of PLC was added and incubated at 37° C. for 20 min with shaking at 500 rpm
4. To 200 μl of spiked blood, 20 μl of PLC was added and incubated at 37° C. for 20 min with shaking at 500 rpm
5. After incubation, 500 μl or 150 μl of HL-SAN buffer was added to 1 ml or
200 μl samples respectively, followed by 10 μl or 3 μl of HL-SAN DNase for 1 ml or 200 μl respectively, mixed briefly by vortexing then incubated at 37° C. for 15 min
6. Samples were centrifuged for 10 min at 12,000×g
7. The supernatant was carefully decanted and the pellet was re-suspended in
200 μl of PBS
8. HL-SAN DNase was inactivated by heat killing at 68° C. for 10 min
9. DNA was extracted from all samples and qPCR was used to quantify human, *E. coli* and *S. aureus* DNA respectively (as detailed above)

Figure 6A:
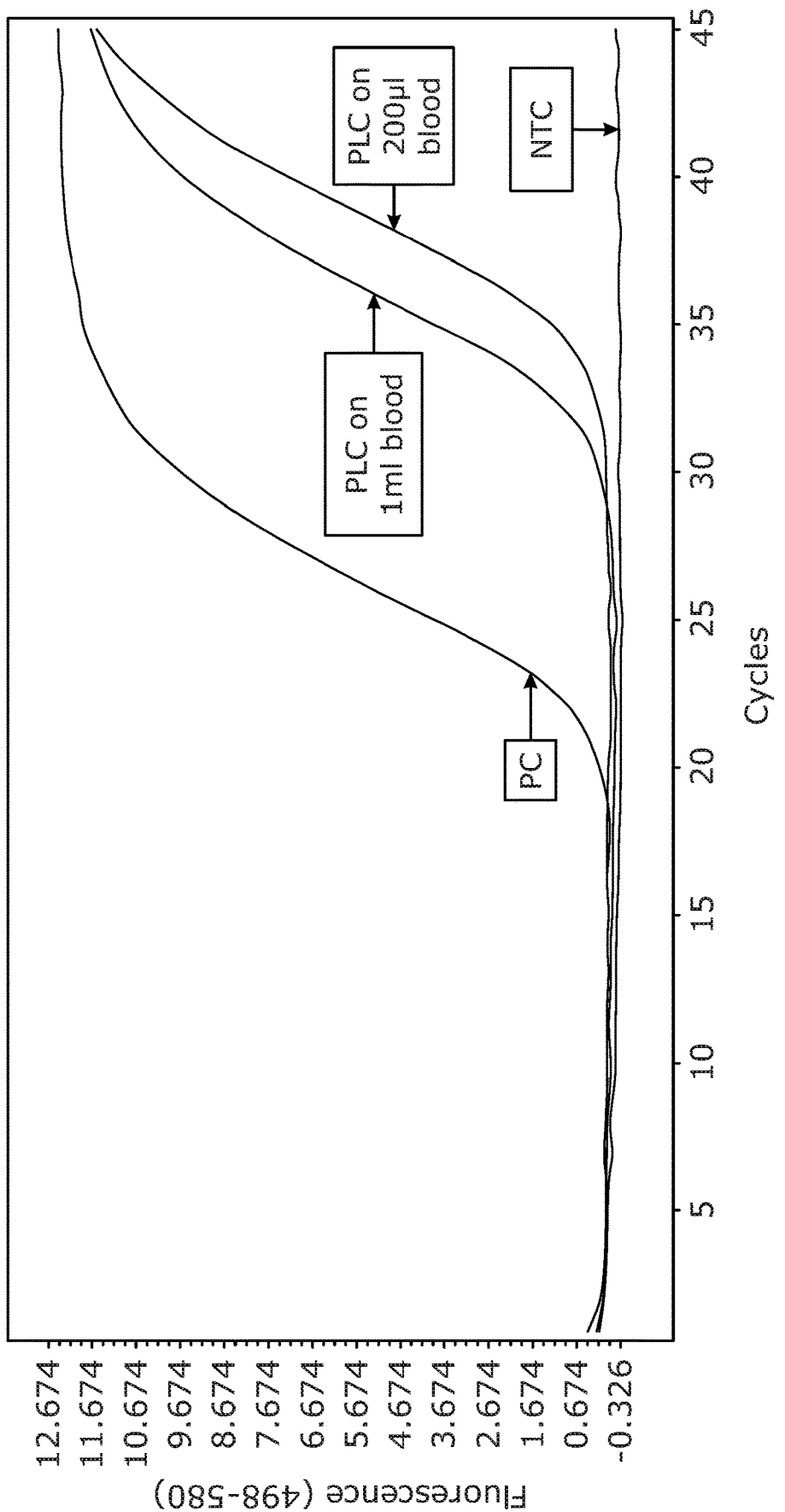
FIG. 6 shows amplification curves of qPCR results after PLC and HL-SAN DNase treatment on increased volumes of bacterial spiked blood; A: Human qPCR; B: *E. coli* qPCR; C: *S. aureus* qPCR.
Figure 6B:
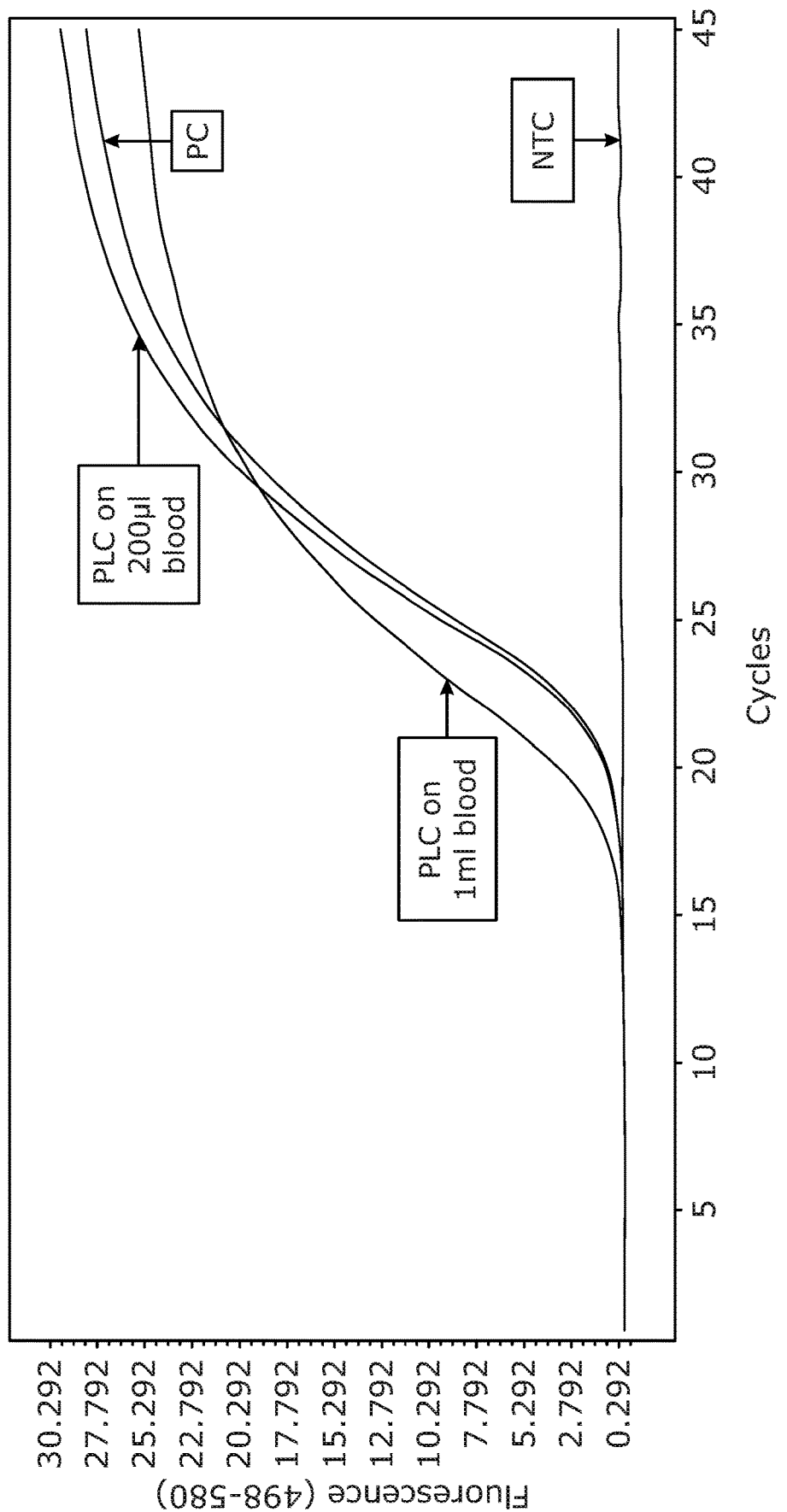
Figure 6C:
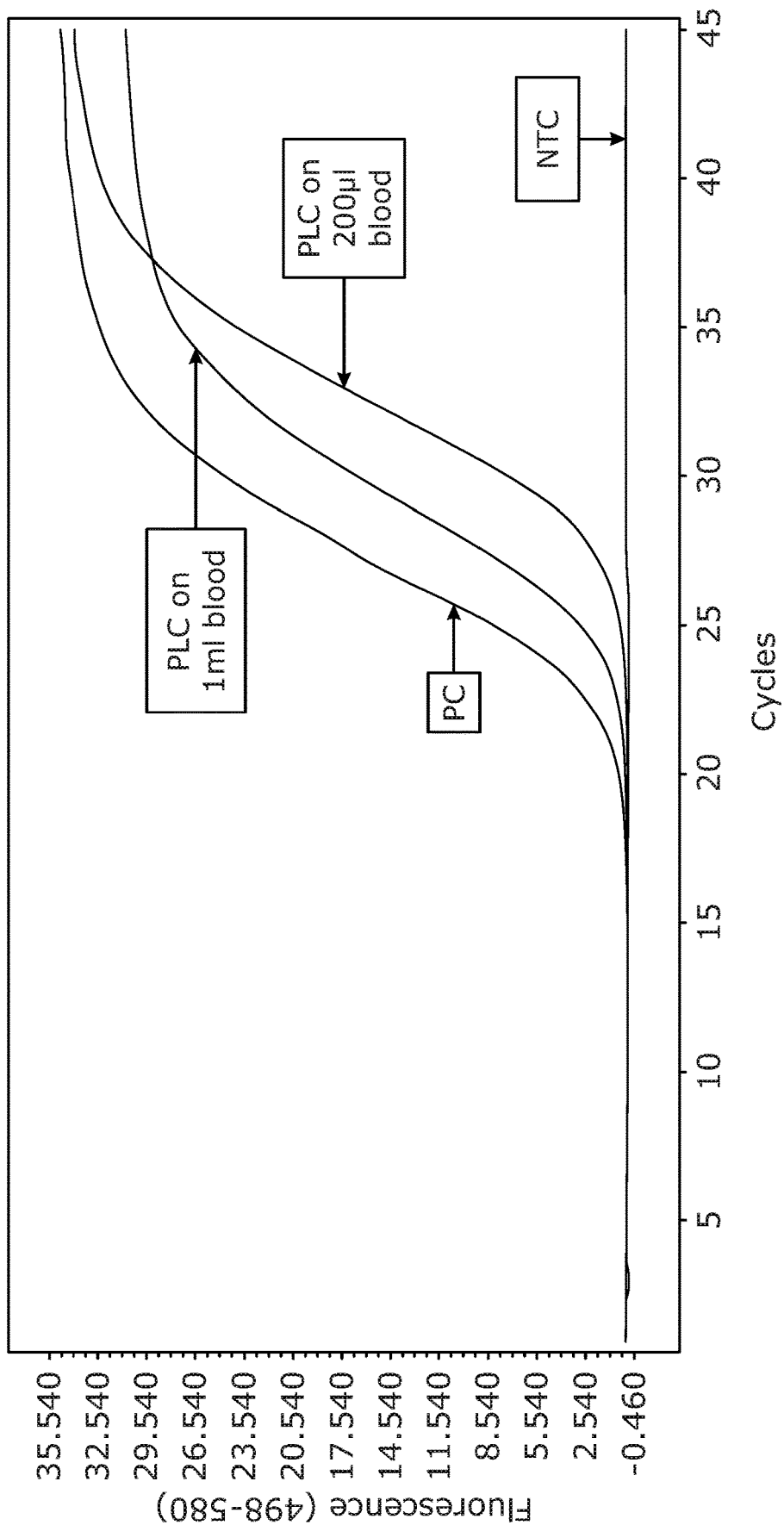

Results:

Increasing the volume of blood resulted in less efficient human DNA depletion (Table 6 and FIG. 6A). There was approximately 4-fold more human DNA remaining in 1 ml of blood compared with 200 µl of blood (ΔCq2). There was no loss of *E. coli* between the two volumes, with the 1 ml sample showing an approximate 5-fold increase in *E. coli* DNA (ΔCq~2.5) as expected (Table 6 and FIG. 6B). There was, however, loss of *S. aureus* DNA in the 200 µl and 1 ml samples, equivalent to approx. 100 fold reduction (ΔCq~6 in the 200 µl sample [lower in the 1 ml sample due to the 5 fold increase in volume tested compared to the PC]) (Table 6 and FIG. 6C).

TABLE 6

Human, *E. coli* and *S. aureus* qPCR results after PLC and HL-SAN DNase treatment on increased volumes of bacteria spiked blood

| Sample ID | Human qPCR (Cq) | *E. coli* qPCR (Cq) | *S. aureus* qPCR (Cq) |
|---|---|---|---|
| PLC on 1 ml blood | 32.11 | 18.72 | 24.97 |
| PLC on 200 µl blood | 34.74 | 21.47 | 28.26 |
| PC | 22.20 | 21.54 | 22.89 |
| NTC | — | — | — |

Conclusion:

Increasing the volume of blood resulted in less efficient human DNA depletion. Loss of *S. aureus* DNA was observed suggesting PLC activity on Gram-positive cell walls or a reduction in *S. aureus* lysis efficiency compared to the PC (possibly due to heat deactivation of DNase). There was no loss of *E. coli* DNA confirming the Gram-negative bacterial cells were not lysed by PLC. We proceeded to attempt to improve the efficiency of human DNA depletion in 1 ml of blood by ensuring effective mixing during incubation with PLC (Example 7). The loss of *S. aureus* was also investigated using the hypothesis that heat inactivation of HL-SAN DNase was affecting the cell wall of *S. aureus*, reducing the efficiency of cell lysis (Example 8).

Example 7—Investigation Mixing During Targeted Cell Lysis in Increased Volumes of Blood Firstly, to investigate the loss of PLC efficiency on host cell lysis in 1 ml of blood, we investigated the effect of efficient mixing. After the addition of PLC to the bacterial spiked blood, samples were aliquoted in larger volume sample tubes (5 ml) and continuously mixed during the incubation period to enhance contact of PLC with the host cells present in the sample and increase lysis efficiency. HL-SAN DNase (plus HL-SAN buffer) was added to enable host DNA depletion and incubated, followed by heat inactivation. A PC sample was included and DNA was extracted from all samples, followed by qPCR for human, *E. coli* and *S. aureus* DNA (as detailed above).

Detailed Procedure:
1. PLC (4 mg) was reconstituted in 100 µl of molecular grade water (40 µg/µl)
2. Blood spiked with *E. coli* and *S. aureus* cultures was aliquoted into 1× 1 ml (in a 5 ml tube) and 1× 200 µl samples
3. To 1 ml of spiked blood, 100 µl of PLC was added and incubated at 37° C. for 20 min with slow mixing using a Hulamixer®
4. To 200 µl of spiked blood, 20 µl of PLC was added and incubated at 37° C. for 20 min with shaking at 500 rpm
5. After incubation, 500 µl or 150 µl of HL-SAN buffer was added to 1 ml or 200 µl samples respectively, followed by 10 µl or 3 µl of HL-SAN DNase for 1 ml or 200 µl respectively, mixed briefly by vortexing then incubated at 37° C. for 15 min
6. Samples were centrifuged for 10 min at 12,000×g
7. The supernatant was carefully decanted and the pellet was re-suspended in 200 µl of PBS
8. HL-SAN DNase was inactivated by heat killing at 68° C. for 10 min
9. DNA was extracted from all samples (including PC) and qPCR was used to quantify human, *E. coli* and *S. aureus* DNA respectively (as detailed above)

Figure 7:
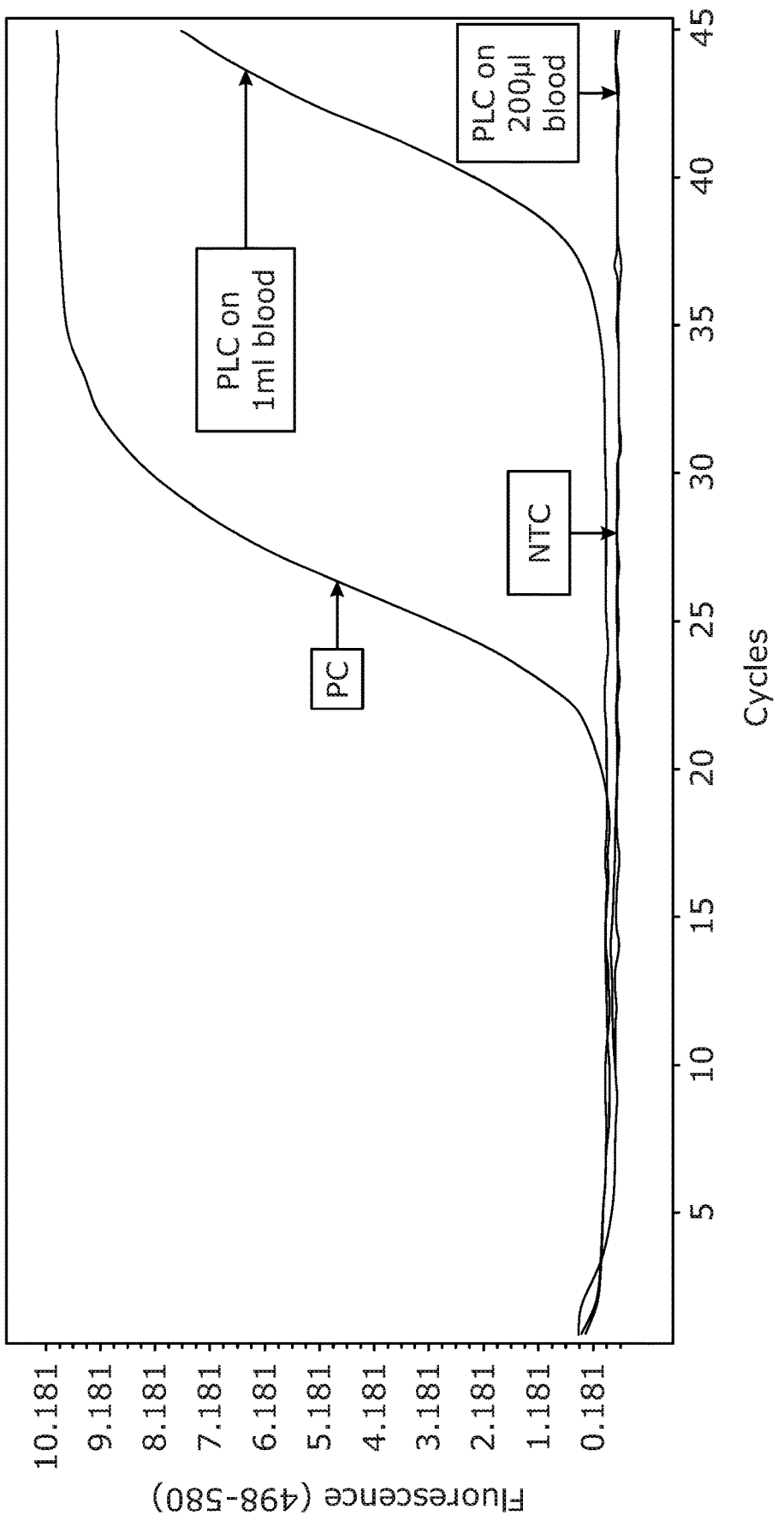
FIG. 7 shows amplification curves of human qPCR results of PLC activity after the addition of efficient mixing during host cell lysis.

Results:

The introduction of a larger sample tube and slow mixing after the addition of PLC resulted in almost complete removal of human DNA (approximately 1 cell human DNA remaining; a depletion of ~$2.6 \times 10^5$ fold (Table 7 and FIG. 7) for the 1 ml sample and complete removal of human DNA for the 200 µl sample (a depletion of at least $10^6$ fold).

TABLE 7

Human qPCR results of PLC activity after the addition of efficient mixing during host cell lysis

| Sample ID | Human qPCR (Cq) |
|---|---|
| PLC on 1 ml blood | 38.04 |
| PLC on 200 µl blood | — |
| PC | 22.38 |
| NTC | — |

Conclusion:

By ensuring efficient mixing during host cell lysis the activity of PLC was improved and provided the level of depletion necessary for detecting pathogen sequences in blood by sequencing. However, as described in Example 6, the loss of *S. aureus* DNA still needed to be investigated (detailed in Example 8).

Example 8—Altered Inactivation of HL-SAN DNase to Improve Gram-Positive Bacterial DNA Recovery We hypothesised that heat inactivation of HL-SAN DNase was affecting the cell wall of *S. aureus*, reducing the efficiency of cell lysis, resulting in low recovery levels of DNA. The aim of this experiment was to try a new method of inactivating HL-SAN DNase in order to improve recovery of *S. aureus* DNA. Rather than heat inactivation of HL-SAN, we inactivated the DNase by removing the high salt conditions required for its activity. PLC was added to bacterial spiked blood samples, incubated and mixed slowly. HL-SAN DNase (+HL-SAN buffer) was added to enable host DNA depletion and incubated. Samples were centrifuged to pellet the intact bacterial cells and the supernatant containing high salt buffer was removed. A PC sample was included and DNA was extracted from all samples, followed by qPCR for human, *E. coli* and *S. aureus* DNA (as detailed above).

Detailed Procedure:
1. PLC (4 mg) was reconstituted in 100 µl of molecular grade water (40 µg/µl)

2. Blood spiked with E. coli and S. aureus cultures was aliquoted into 1× 1 ml (in a 5 ml tube) and 1× 200 μl samples
3. To 1 ml of spiked blood, 100 μl of PLC was added and incubated at 37° C. for 20 min with slow mixing using a Hulamixer®
4. To 200 μl of spiked blood, 20 μl of PLC was added and incubated at 37° C. for 20 min with shaking at 500 rpm
5. After incubation, 500 μl or 150 μl of HL-SAN buffer was added to 1 ml or 200 μl samples respectively, followed by 10 μl or 3 μl of HL-SAN DNase for 1 ml or 200 μl respectively, mixed briefly by vortexing then incubated at 37° C. for 15 min
6. Samples were centrifuged for 10 min at 12,000×g
7. The supernatant was carefully decanted and the pellet was re-suspended in 1.5 ml PBS
8. Prior to DNA extraction, bacterial cells were pelleted by centrifuging at 12000×g for 5 min
9. DNA was extracted from all samples (including PC) and qPCR was used to quantify human, E. coli and S. aureus DNA respectively (as detailed above)

Figure 8A:
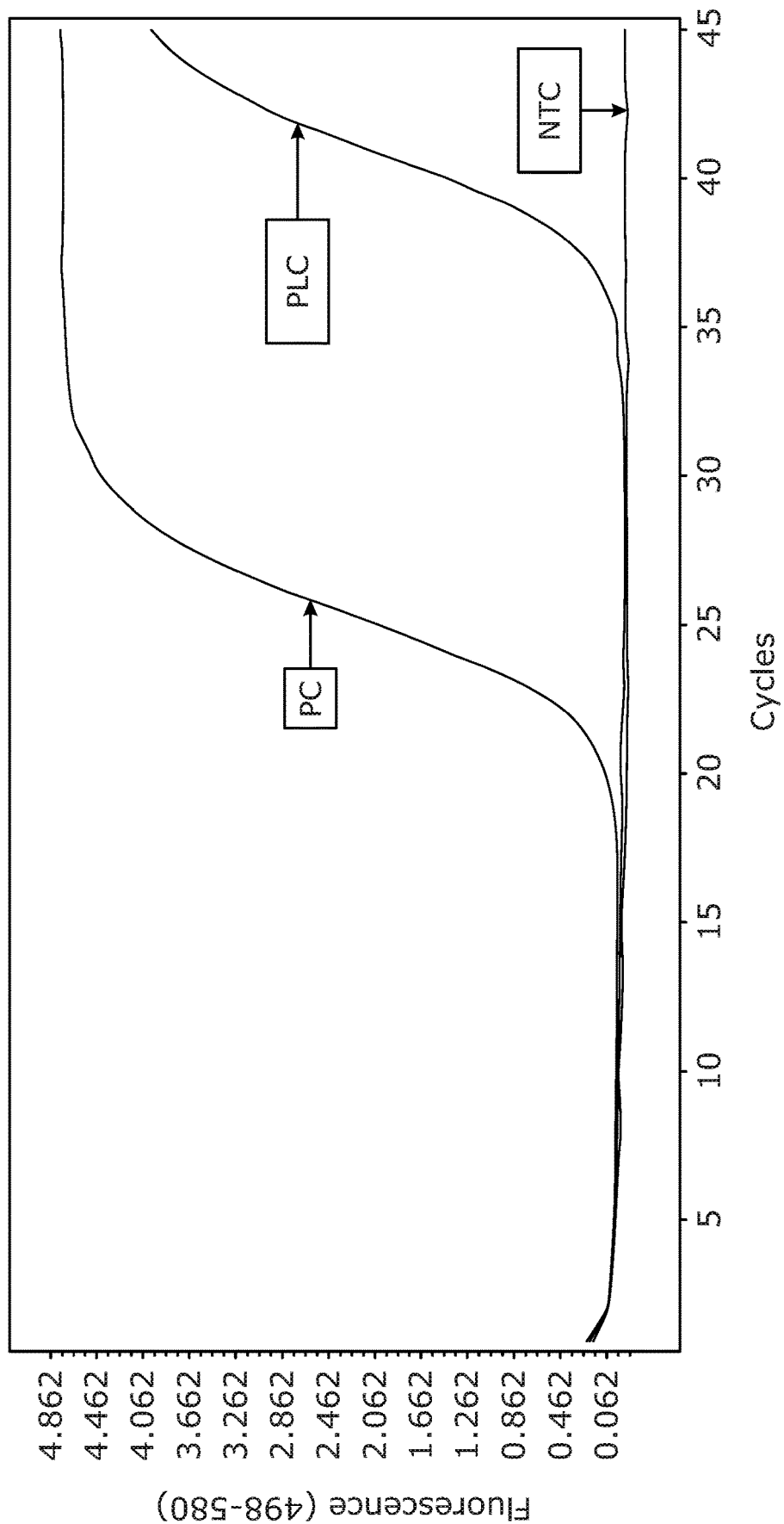
FIG. 8 shows amplification curves of qPCR results after altered HL-SAN DNase inactivation; A: Human qPCR; B: *E. coli* qPCR; C: *S. aureus* qPCR.
Figure 8B:
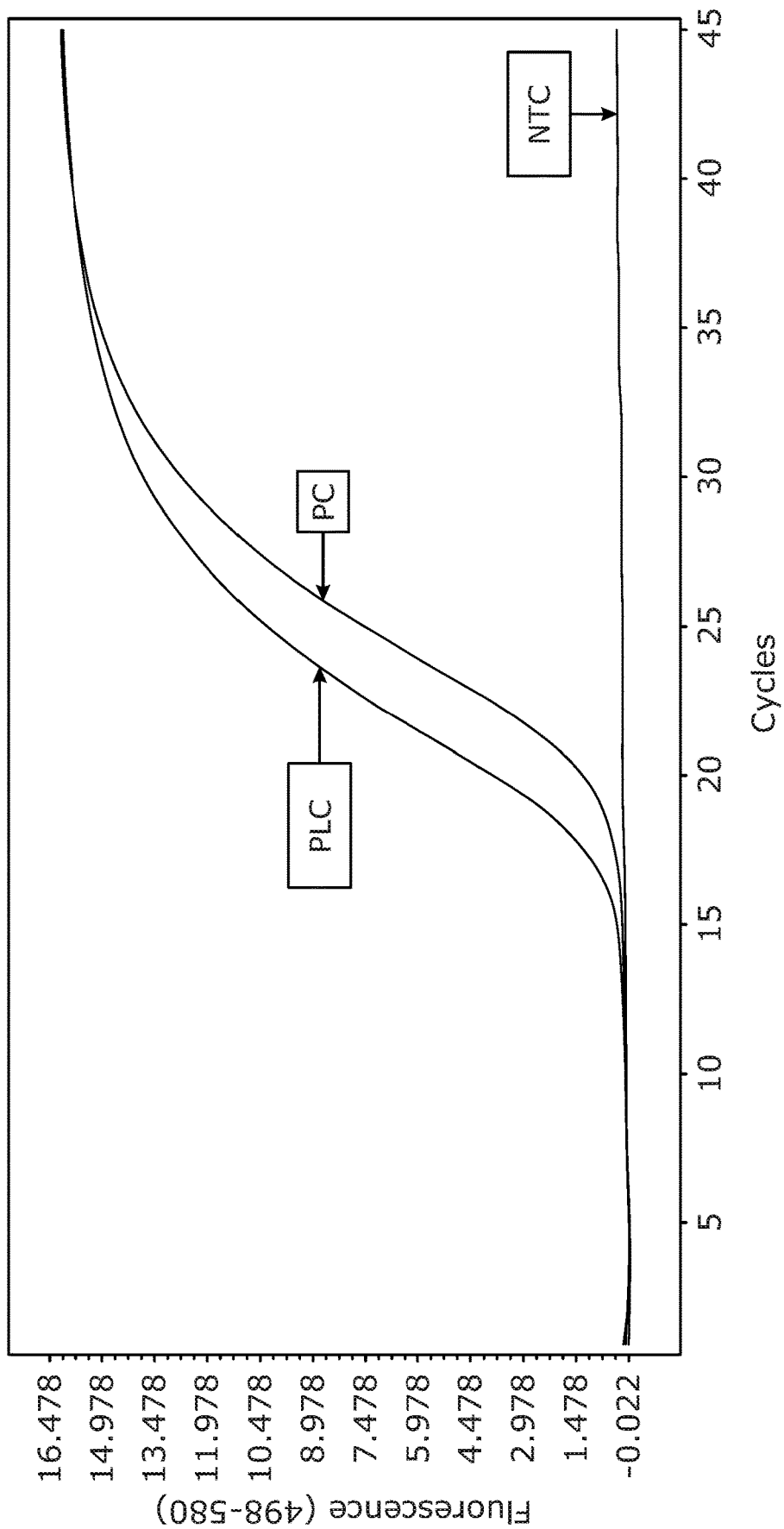
Figure 8C:
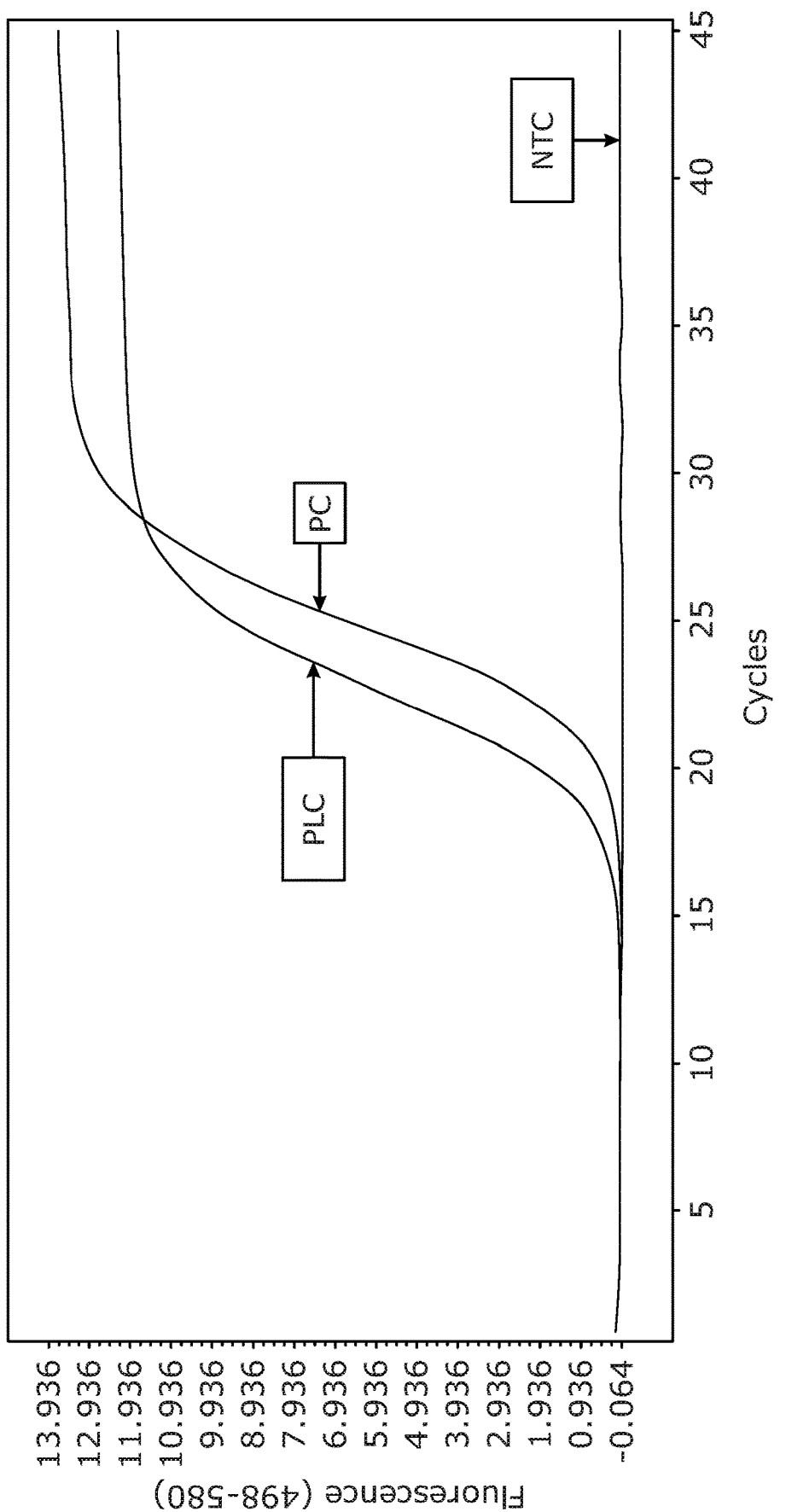

Results:

Using buffer exchange rather than heat inactivation on HL-SAN DNase resulted in efficient human DNA depletion with no loss of E. coli or S. aureus DNA (Table 8 and FIG. 8). Human DNA depletion was effectively ~2.3×10$^5$ fold when using a 1 ml sample and (data not shown) at least 10$^6$ fold when using a 200 μl sample (no human DNA detected).

TABLE 8

Human, E. coli and S. aureus qPCR results after altered HL-SAN DNase inactivation

| Sample ID | Human qPCR (Cq) | E. coli qPCR (Cq) | S. aureus qPCR (Cq) |
|---|---|---|---|
| PLC | 37.36 | 17.65 | 19.04 |
| PC | 21.90 | 20.17 | 21.47 |
| NTC | — | — | — |

Conclusion:

Introducing a buffer exchange to inactivate HL-SAN DNase instead of heat inactivation, improved the lysis efficiency of S. aureus cells (it is likely that this could also have been achieved by using a more robust lysis method such as bead beating or using an enzyme cocktail). This method alteration enabled efficient S. aureus DNA recovery with no negative effect on E. coli DNA recovery (previously reported in Example 6) or on human DNA depletion (previously reported in Example 7). Hence an efficient cytolysin human DNA depletion procedure had been developed that did not result in the loss of the microbial component of the sample. In order to confirm the robustness of this procedure we compared it to the commercially available MolYsis® method and our in-house modified MolYsis® procedure (Example 9).

Example 9—Comparison of Cytolysin Human DNA Depletion Against MolYsis® Basic 5 Kit and a Modified MolYsis® Method To test the robustness of our newly developed human DNA depletion procedure we compared it to the commercially available MolYsis® pathogen DNA isolation protocol and an in-house modified MolYsis® protocol. Our cytolysin human DNA depletion procedure was carried out as per Example 8 using the buffer exchange method rather than heat inactivation of HL-SAN DNase. The MolYsis® pathogen DNA isolation protocol was performed as detailed in the manufacturer's instructions. A modified MolYsis® protocol (developed in house) was also tested which initially removed leukocytes by immunomagnetic separation, followed by MolYsis® as per the manufacturer's instructions.

Method 1 (Cytolysin human DNA depletion): As described in Example 8.

Method 2 (MolYsis®):

MolYsis® was used as per the manufacturer's instructions.

Method 3 (Modified MolYsis®):
1. Anti-CD45 coated magnetic beads were re-suspended by gentle mixing then the desired volume of beads (250 μl per 1 ml sample) was aliquoted
2. Beads were washed by re-suspending in 1 ml of isolation buffer (25 ml Ca$^{2+}$·Mg$^{2+}$ free PBS, 100 μl 0.5M EDTA and 0.025 g BSA)
3. Beads were separated on a magnetic rack and the supernatant was discarded
4. Beads were re-suspended in 250 μl of isolation buffer
5. Leukocytes were depleted by adding 250 μl of washed beads to 1 ml of blood and mixed gently at 2-8° C. for 30 min using a Hulamixer®
6. Beads were separated on a magnetic rack and the supernatant was transferred to a new sterile tube
7. Intact bacterial cells and any remaining blood cells were pelleted by centrifugation at 12,000×g for 10 min then the supernatant was discarded
8. The pellet was re-suspended in 1 ml PBS
9. Samples were further processed using the MolYsis® protocol according to the manufacturer's instructions DNA was extracted from all samples (including PC) and qPCR was used to quantify human, E. coli and S. aureus DNA respectively for all methods (as detailed above)

Figure 9A:
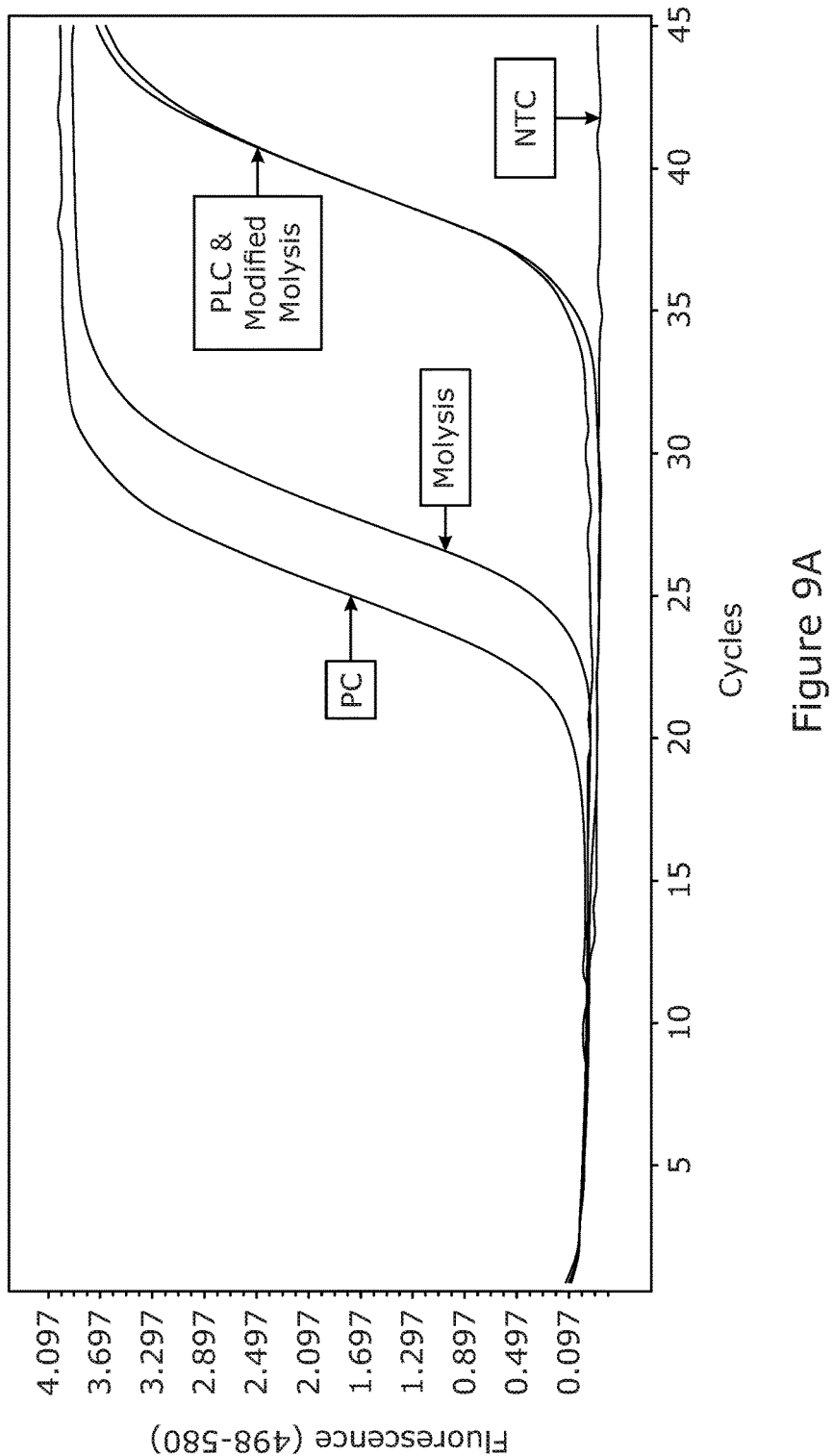
FIG. 9 shows Amplification curves of qPCR results for method comparison; A: Human qPCR; B: *E. coli* qPCR; C: *S. aureus* qPCR.
Figure 9B:
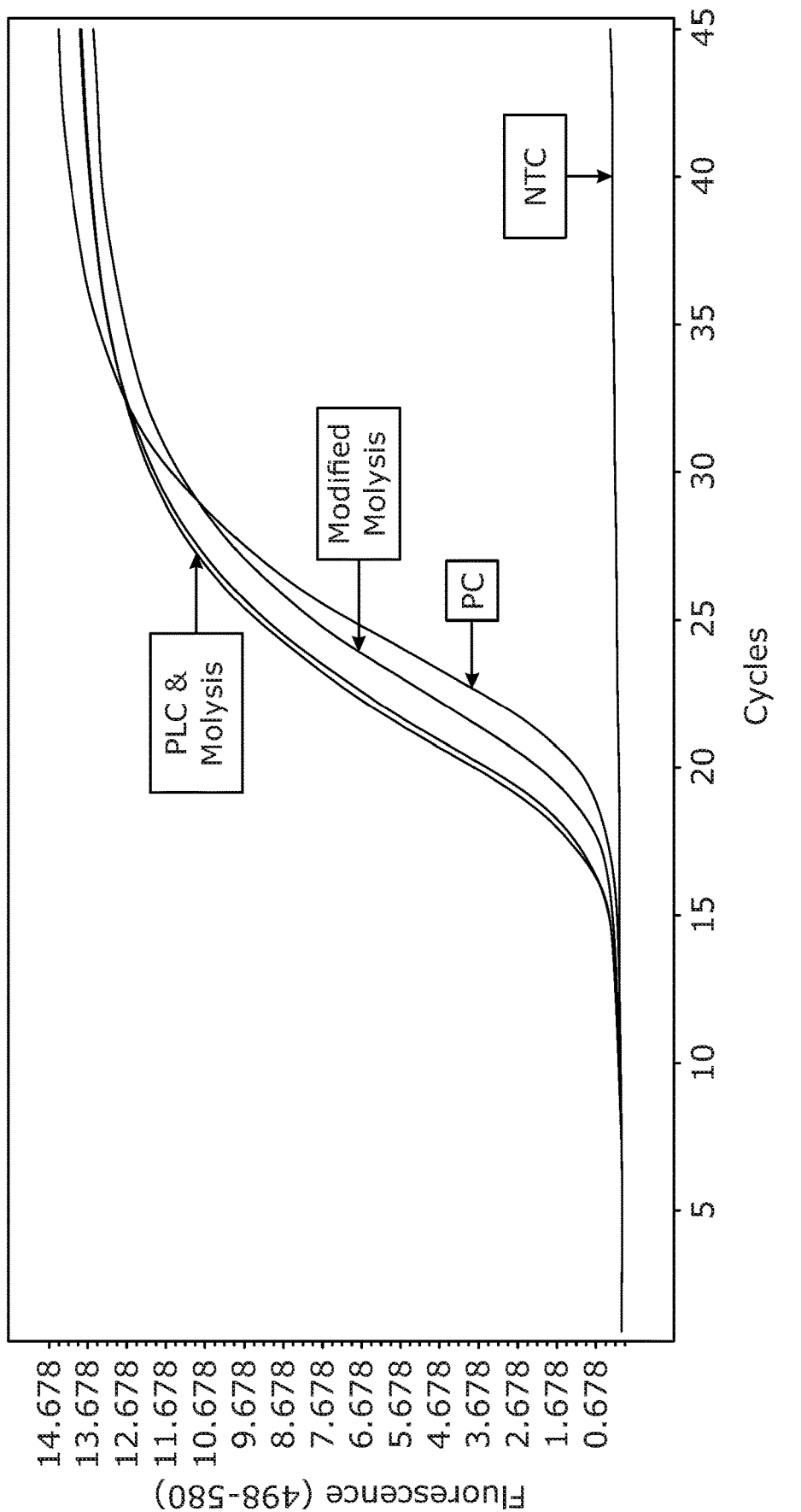
Figure 9C:
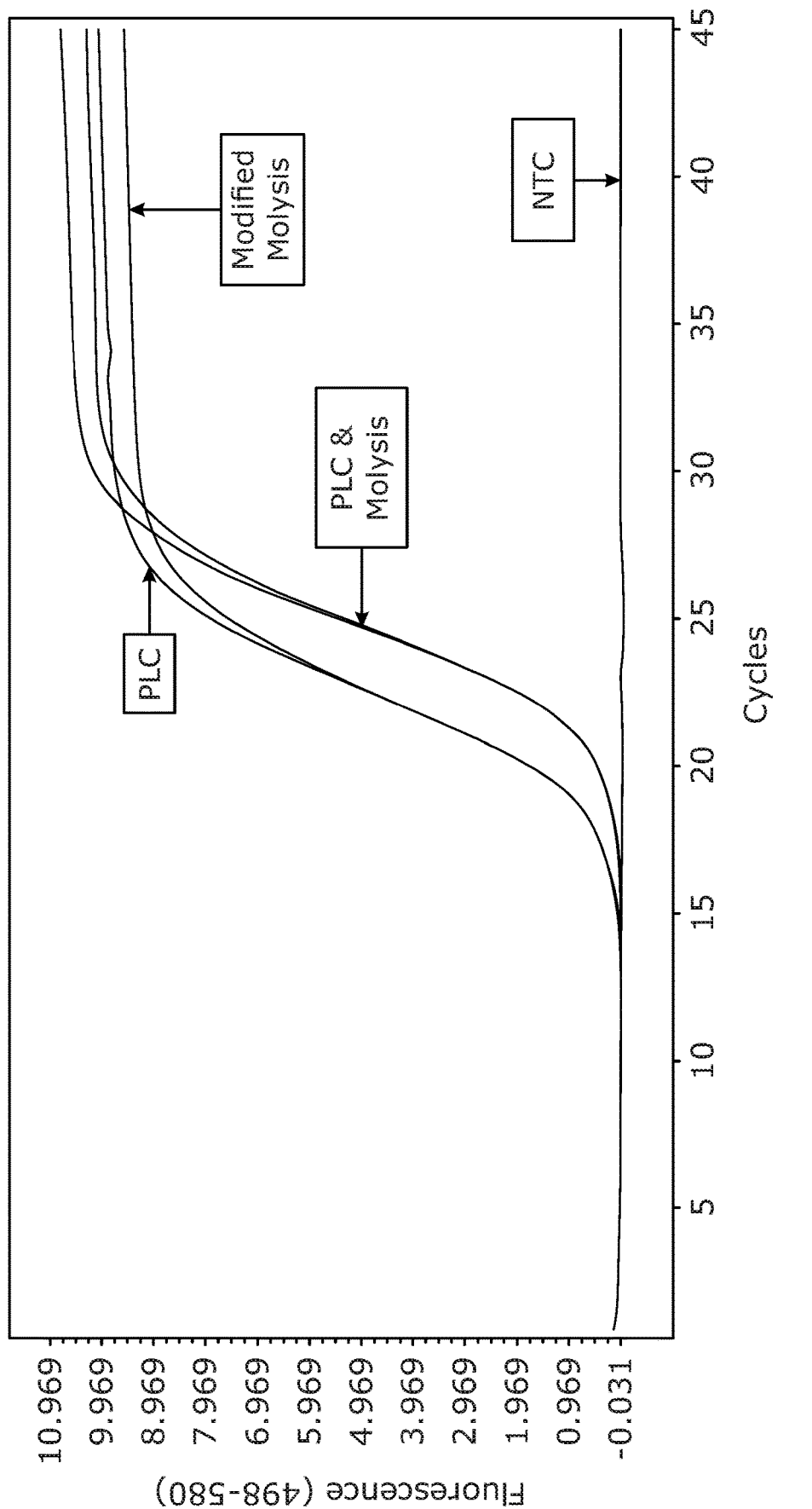

Results:

When comparing our human DNA depletion method to commercially available MolYsis® we observed approximately 10$^4$-fold more human DNA depletion (ΔCq12) and comparable levels of bacterial DNA recovery (Table 9 and FIG. 9). Our modified MolYsis® protocol also showed an approximate 10$^4$-fold reduction in human DNA (ΔCq12) compared to MolYsis®.

TABLE 9

Human, E. coli and S. aureus qPCR results for method comparison

| Sample ID | Human qPCR (Cq) | E. coli qPCR (Cq) | S. aureus qPCR (Cq) |
|---|---|---|---|
| PLC | 36.05 | 17.58 | 18.98 |
| Modified MolYsis (RTM) | 36.13 | 18.74 | 18.89 |
| MolYsis (RTM) | 24.54 | 17.25 | 21.33 |
| PC | 21.87 | 20.13 | 21.31 |
| NTC | — | — | — |

Conclusion:

In comparison to the commercially available MolYsis® kit, our human DNA depletion method was more efficient at human DNA depletion (showing 9.3×10$^4$ fold depletion of human DNA). Only our modified MolYsis® protocol showed the same level of efficiency compared to our cytolysin human DNA depletion method. This demonstrates that the leading commercially available host depletion kit does not provide sufficient host cell/DNA depletion to enable efficient pathogen DNA detection by sequencing.

Overview:

In conclusion, we have developed a rapid pathogen identification procedure which utilizes the properties of cytolysins (PLC) and endonucleases (HL-SAN DNase) to specifically target and lyse host cells present in clinical samples (i.e. blood), followed by DNA digestion. This procedure is a pre-step to enable sufficient pathogen DNA extraction for NGS. As blood represents the most complex clinical sample matrix type with extremely high human to bacterial cell ratios, we predict that the clinical sample type will be easily interchangeable without affecting the levels of human DNA depletion.

After a number of methodology alterations, the finalised procedure is detailed below.

Initially Optimised Human DNA Depletion Method

PLC solution: 4 mg in 100 µl nuclease free water

HL-SAN buffer: 10 mM Tris HCL, 100 mM Magnesium and 1M NaCl pH8.5 in nuclease free water 100 µl PLC solution was added to 1 ml blood

↓

Incubated at 37° C. with gentle mixing for 20 min

↓

500 µl HL-SAN buffer, 10 µl HL-SAN DNase was added and mixed by vortexing, then incubated at 37° C. for 15 min

↓

Bacterial cells were pelleted at 12,000×g for 10 min

↓

Supernatant was discarded

↓

Bacterial cell pellet was resuspended in 1.5 ml PBS

↓

Pellet bacterial cells at 12,000×g for 5 mins and remove supernatant

↓

Proceeded to DNA extraction of choice

[Total time: 50 min.]

DNA Extraction

Bacterial cell pellet was resuspended in 350 µl bacterial lysis buffer and vortexed

↓

30 µl enzyme cocktail (lysozyme, mutanolysis and lysostaphin—lyticase optional) was added and incubated at 37° C. for 15 min at 1000 rpm

↓

20 µl proteinase K was added

↓

Mixed by vortexing

↓

Incubated at 65° C. for 5 min

↓

Proceed to MagNAPure® (Roche) for DNA extraction

[Total time: 45 min.]

[Therefore current protocol turnaround time approximately 90 min.]

Example 10—Verification of Methodology for Fungal Enrichment 10.1: The protocol above was altered slightly to focus on fungal enrichment and the final protocol was carried out to verify bacterial enrichment. The protocol was tested using ~200 E. coli cells. Blood was spiked with ~200 E. coli cells and was processed as detailed in section 10.2.

10.2: Amended protocol ("Enrichment" procedure):

1 PLC was added (0.8 mg/20 µl) to the blood sample (200 µl), vortexed and incubated at 37° C. for 15 min at 1000 RPM in a heatblock.

2 HL-SAN buffer (5M NaCl and 100 mM $MgCl_2$) was added at a 1:1 volume ratio (200 µl) with 10 µl HL-SAN DNase, vortexed and incubated at 37° C. for 15 min at 1000 RPM in a heat block.

3 PBS was added to a total volume of 2 ml (1.5 ml).

4 Cells were pelleted by centrifugation at 12,000×g for 10 min and the supernatant was discarded.

5 The cell pellet was resuspended in 1.5 ml PBS.

6 Cells were pelleted again by centrifugation at 12,000×g for 10 min and the supernatant was discarded.

7 To any test samples; 350 µl bacterial lysis buffer, 20 µl enzyme cocktail (6 µl mutanolysin 25 ku/ml, 5 µl lysozyme 10 mg/ml, 4 µl lyticase 10 ku/ml, 3 µl lysostaphin 4 ku/ml, 2 µl chitinase 50 u/ml) and 5 µl RNase A was added.

8 All samples were incubated at 37° C. for 15 min at 1000 RPM in a heat block.

9 To all samples, 20 µl proteinase K was added and incubated at 65° C. for 10 min in a heat block.

10 Total nucleic acid was extracted using the MagnaPure® Compact automated machine using the DNA_bacteria_V3_2 protocol.

11 Host DNA/RNA depletion and fungal DNA enrichment was determined via qPCR or RT-qPCR.

Results:

After plate counts it was identified that 200 µl of blood was spiked with ~110 E. coli cells. This resulted in ~$10^5$ fold depletion of human DNA and no loss of E. coli DNA (Tables 10.1a/b).

TABLE 10.1a

Human DNA qPCR results for ~110 E. coli cells spiked blood with and without fungal/bacterial enrichment.

| Sample ID | Human qPCR assay (Cq) | ΔCq against PC |
|---|---|---|
| PC blood spiked | 22.72 | 17.3 |
| Blood spiked Enriched (Sample 1) | Undetectable | |

TABLE 10.1b

E. coli DNA qPCR results for ~110 E. coli cells spiked blood with and without fungal/bacterial enrichment.

| Sample ID | E. coli qPCR assay (Cq) | ΔCq against PC |
|---|---|---|
| PC blood spiked | 36.88 | 0.9 |
| Blood spiked Enriched (Sample 1) | 37.78 | |

Whole blood was spiked with ~1000 C. albicans cells and two samples were processed as detailed in section 10.2. After the enrichment protocol there was between ~$10^4$ and ~$10^5$ fold depletion of human DNA and no loss of C. albicans DNA (Tables 10.2a/b).

TABLE 10.2a

Human DNA qPCR results in duplicate for ≤1000 *C. albicans* cells spiked blood with and without bacterial/fungal enrichment.

| Sample ID | Human qPCR assay (Cq) | Average Human (Cq) | Average ΔCq against PC |
|---|---|---|---|
| PC blood spiked (PC 1) | 24.37 | 24.3 | 14.9 |
| PC blood spiked (PC 2) | 24.32 | | |
| Blood spiked Enriched (Sample 1) | Undetectable (>40) | 39.2 | |
| Blood spiked Enriched (Sample 2) | 38.33 | | |

TABLE 10.2b

*C. albicans* DNA qPCR results in duplicate for ≤1000 *C. albicans* cells spiked blood with and without bacterial/fungal enrichment.

| Sample ID | *C. albicans* qPCR assay (Cq) | Average *C. albicans* (Cq) | Average ΔCq against PC |
|---|---|---|---|
| PC blood spiked (PC 1) | 33.91 | 33.6 | 2.3 |
| PC blood spiked (PC 2) | 33.28 | | |
| Blood spiked Enriched (Sample 1) | 30.81 | 31.3 | |
| Blood spiked Enriched (Sample 2) | 31.81 | | |

Whole blood was then spiked with ~200 *C. albicans* cells and was processed as detailed in section 10.2. After plate counts of *C. albicans* on sabouraud agar, it was identified that 200 µl of blood was spiked with ~60 *C. albicans* cells. After the enrichment protocol this resulted in ~$10^5$ fold depletion of human DNA and no loss of *C. albicans* DNA (Tables 10.3a/b).

TABLE 10.3a

Human DNA qPCR results in for ~60 *C. albicans* cells spiked blood with and without bacterial/fungal enrichment.

| Sample ID | Human qPCR assay (Cq) | ΔCq against PC |
|---|---|---|
| PC blood spiked | 24.8 | 15.2 |
| Blood spiked Enriched (Sample 1) | 40 | |

TABLE 10.3b

*C. albicans* DNA qPCR results in for ~60 *C. albicans* cells spiked blood with and without bacterial/fungal enrichment.

| Sample ID | *C. albicans* qPCR assay (Cq) | ΔCq against PC |
|---|---|---|
| PC blood spiked | 35.55 | 3.3 |
| Blood spiked Enriched (Sample 1) | 32.22 | |

Using the *A. niger* bioball known to be ~$10^8$ cfu/ml, serial dilutions were made to ~$10^4$ and ~$10^3$. Both samples were processed as described in section 10.2. After the enrichment protocol this resulted in ~$10^5$ fold depletion of human DNA and no loss of *A. niger* DNA (Tables 10.4a-b/10.5a-b).

TABLE 10.4a

Human DNA qPCR results for ~200 *A. niger* cells ($10^3$ dilution) spiked blood with and without bacterial/fungal enrichment.

| Sample ID | Human qPCR assay (Cq) | ΔCq against PC |
|---|---|---|
| PC blood spiked (PC 1) | 22.91 | 14.71 |
| Blood spiked Enriched (Sample 1) | 37.62 | |

TABLE 10.4b

*A. niger* DNA qPCR results for ~200 *A. niger* cells ($10^3$ dilution) spiked blood with and without bacterial/fungal enrichment.

| Sample ID | *A. niger* qPCR assay (Cq) | ΔCq against PC |
|---|---|---|
| PC blood spiked (PC 1) | 39.21 | 0.79 |
| Blood spiked Enriched (Sample 1) | 40 | |

TABLE 10.5a

Human DNA qPCR results for ~2,000 *A. niger* cells ($10^4$ dilution) spiked blood with and without bacterial/fungal enrichment.

| Sample ID | Human qPCR assay (Cq) | Average ΔCq against PC |
|---|---|---|
| PC blood spiked (PC 2) | 22.54 | 13.39 |
| Blood spiked Enriched (Sample 2) | 35.93 | |

TABLE 10.5b

*A. niger* DNA qPCR results for ~2,000 *A. niger* cells ($10^4$ dilution) spiked blood with and without bacterial/fungal enrichment.

| Sample ID | *A. niger* qPCR assay (Cq) | Average ΔCq against PC |
|---|---|---|
| PC blood spiked (PC 2) | 34.62 | 1.95 |
| Blood spiked Enriched (Sample 2) | 36.57* | |

*Cq value suggests < 10 cell (<100 cells in total input)

Conclusion: Using the protocol detailed in section 10.2, there is ~$10^5$ fold human DNA depletion with no loss of bacterial or fungal DNA.

Example 11—Verification of Methodology for Virus and Phage Enrichment 11.1: Protocol for Viral Enrichment in Plasma
1. Whole blood was spiked with viral particles (max 200 µl per sample).
2. Samples were centrifuged at 20,000×g for 5 min.

3. Supernatant was retained and used for the protocol (effectively working in plasma) after being aliquoted into equal volumes (max 200 μl).
4. 20 μl of PLC (0.8 mg) was added to each test sample and incubated at 37° C. for 15 min with shaking at 1000 RPM in a heat-block.
5. 200 μl of HL-SAN buffer (5 M NaCl and 100 mM $MgCl_2$) and 10 μl HL-SAN was added, incubated at 37° C. for 15 min with shaking at 1000 RPM in a heat-block.
6. 20 μl proteinase K was added to all samples and incubated at 65° C. for 10 min.
7. Total nucleic acid was extracted using the MagnaPure® Compact automated machine using the DNA_bacteria_V3_2 protocol.
8. Host DNA/RNA depletion and viral DNA/RNA enrichment was determined via qPCR or RT-qPCR.

11.2: Protocol for Viral Enrichment in Blood
1. Whole blood was spiked with viral particles (max 200 μl per sample).
2. 20 μl of PLC (0.8 mg) was added to each test sample and incubated at 37° C. for 15 min with shaking at 1000 RPM in a heat-block.
3. 200 μl of HL-SAN buffer (5 M NaCl and 100 mM $MgCl_2$) and 10 μl HL-SAN was added, incubated at 37° C. for 15 min with shaking at 1000 RPM in a heat-block.
4. Test samples were centrifuged at 20,000×g for 5 min and the supernatant retained.
5. 20 μl proteinase K was added to all samples and incubated at 65° C. for 10 min.
6. Total nucleic acid was extracted using the MagnaPure® Compact automated machine using the DNA_Bacteria_V3_2 protocol.
7. Host DNA/RNA depletion and viral DNA/RNA enrichment was determined via qPCR or RT-qPCR.

Once the protocols described in sections 11.1 and 11.2 were established, samples were run in triplicate to access the reproducibility of the protocols (a second blood protocol was also tested at this stage which was the same as section 11.2 with an additional centrifugation step after step 4).

Results:

In total, each 200 μl blood sample was spiked with 10,000 IU HIV and 350 IU HBV. For this experiment, all three enrichment protocols were tested in triplicate (as previously described). After the viral enrichment protocols in blood there was consistently ~$10^4$ fold depletion in human DNA and human DNA was undetectable after enrichment when working in plasma (Tables 11.1a/b).

There was no loss of HBV viral DNA target in blood and plasma, although it should be noted that the number of HBV cells in the PCR reactions was ~35 and so Cq values were close to the limit of detection for the qPCR assay used (Tables 11.2a/b). With regards RNA viral targets, there was no loss of HIV in blood and plasma (Tables 11.3a/b).

TABLE 11.1a

Human DNA qPCR results in triplicate for spiked blood with and without viral enrichment.

| Sample ID | Human qPCR assay (Cq) | Average Human (Cq) | Average ΔCq against PC |
|---|---|---|---|
| PC blood spiked 1 (PC #1) | 24.34 | 24.81 | |
| PC blood spiked 2 (PC #2) | 25.04 | | |

TABLE 11.1a-continued

Human DNA qPCR results in triplicate for spiked blood with and without viral enrichment.

| Sample ID | Human qPCR assay (Cq) | Average Human (Cq) | Average ΔCq against PC |
|---|---|---|---|
| PC blood spiked 3 (PC #3) | 25.06 | | |
| Blood spiked Enriched 1 1 (T_1 #1) | 37.32 | 37.54 | 12.73 ($10^4$) |
| Blood spiked Enriched 1 2 (T_1 #2) | 37.68 | | |
| Blood spiked Enriched 1 3 (T_1 #3) | 37.91 | | |
| Blood spiked Enriched 2 1 (T_2 #1) | 37.94 | 38.16 | 13.35 ($10^4$) |
| Blood spiked Enriched 2 2 (T_2 #2) | 38.64 | | |
| Blood spiked Enriched 2 3 (T_2 #3) | 37.91 | | |

TABLE 11.1b

Human DNA qPCR results in triplicate for spiked plasma with and without viral enrichment.

| Sample ID | Human qPCR assay (Cq) | Average ΔCq against PC |
|---|---|---|
| PC plasma spiked 1 (PC_SN #1) | 34.64 | Undetectable |
| PC plasma spiked 2 (PC_SN #2) | 33.45 | |
| PC plasma spiked 3 (PC_SN #3) | 33.81 | |
| Plasma spiked Enriched 1 (T_SN #1) | Undetectable | |
| Plasma spiked Enriched 2 (T_SN #2) | Undetectable | |
| Plasma spiked Enriched 3 (T_SN #3) | Undetectable | |

TABLE 11.2a

HBV DNA qPCR results in triplicate for spiked blood with and without viral enrichment.

| Sample ID | HBV qPCR assay (Cq) | Average HBV (Cq) | Average ΔCq against PC |
|---|---|---|---|
| PC blood spiked 1 (PC #1) | 38.02 | 37.9 | |

TABLE 11.2a-continued

HBV DNA qPCR results in triplicate for spiked blood with and without viral enrichment.

| Sample ID | HBV qPCR assay (Cq) | Average HBV (Cq) | Average ΔCq against PC |
|---|---|---|---|
| PC blood spiked 2 (PC #2) | 36.95 | | |
| PC blood spiked 3 (PC #3) | 38.76 | | |
| Blood spiked Enriched 1 1 (T_1 #1) | 39.12 | 38 | 0.1 |
| Blood spiked Enriched 1 2 (T_1 #2) | 37.99 | | |
| Blood spiked Enriched 1 3 (T_1 #3) | 36.81 | | |
| Blood spiked Enriched 2 1 (T_2 #1) | 37.37 | 37.4 | 0.5 |
| Blood spiked Enriched 2 2 (T_2 #2) | 37.47 | | |
| Blood spiked Enriched 2 3 (T_2 #3) | Undetectable | | |

TABLE 11.2b

HBV DNA qPCR results in triplicate for spiked plasma with and without viral enrichment.

| Sample ID | HBV qPCR assay (Cq) | Average ΔCq against PC |
|---|---|---|
| PC plasma spiked 1 (PC_SN #1) | 37.62 | 0.02 |
| PC plasma spiked 2 (PC_SN #2) | 36.92 | |
| PC plasma spiked 3 (PC_SN #3) | 36.95 | |
| Plasma spiked Enriched 1 (T_SN #1) | 37.22 | |
| Plasma spiked Enriched 2 (T_SN #2) | Undetectable | |
| Plasma spiked Enriched 3 (T_SN #3) | Undetectable | |

TABLE 11.3a

HIV RNA RT-qPCR results in triplicate for spiked blood with and without viral enrichment.

| Sample ID | HIV qPCR assay (Cq) | Average HIV (Cq) | Average ΔCq against PC |
|---|---|---|---|
| PC blood spiked 1 (PC #1) | 32.76 | 33.2 | |
| PC blood spiked 2 (PC #2) | 33.60 | | |
| PC blood spiked 3 (PC #3) | 33.14 | | |
| Blood spiked Enriched 1 1 (T_1 #1) | 33.33 | 33.5 | 0.3 |
| Blood spiked Enriched 1 2 (T_1 #2) | 34.02 | | |
| Blood spiked Enriched 1 3 (T_1 #3) | 33.08 | | |
| Blood spiked Enriched 2 1 (T_2 #1) | 33.63 | 33.7 | 0.5 |
| Blood spiked Enriched 2 2 (T_2 #2) | 33.75 | | |
| Blood spiked Enriched 2 3 (T_2 #3) | 33.65 | | |

TABLE 11.3b

HIV RNA RT-qPCR results in triplicate for spiked plasma with and without viral enrichment.

| Sample ID | HIV qPCR assay (Cq) | Average HIV (Cq) | Average ΔCq against PC |
|---|---|---|---|
| PC plasma spiked 1 (PC_SN #1) | 34.44 | 34.6 | |
| PC plasma spiked 2 (PC_SN #2) | 33.75 | | |
| PC plasma spiked 3 (PC_SN #3) | 35.64 | | |
| Plasma spiked Enriched 1 (T_SN #1) | 35.66 | 34.9 | 0.4 |
| Plasma spiked Enriched 2 (T_SN #2) | 35.00 | | |
| Plasma spiked Enriched 3 (T_SN #3) | 34.03 | | |

Next, for phage testing; in total, each 200 µl blood sample was spiked with either $10^4$, $10^5$, $10^6$ or $10^7$ phage. After the viral enrichment protocol in plasma (section 11.1) there was consistently ~$10^3$ fold depletion in human DNA with no loss of phage target (Tables 11.4a/b).

TABLE 11.4a

Human DNA qPCR results for spiked blood with and without viral enrichment.

| Sample ID | Human qPCR assay (Cq) | Average ΔCq against PC |
|---|---|---|
| PC blood spiked $10^4$ | 28.01 | 11.99 |
| Blood spiked Enriched $10^4$ | 40 | |
| PC blood spiked $10^5$ | 28.68 | 11.32 |
| Blood spiked Enriched $10^5$ | 40 | |
| PC blood spiked $10^6$ | 28.72 | 11.28 |
| Blood spiked Enriched $10^6$ | 40 | |
| PC blood spiked $10^7$ | 28.43 | 9.52 |
| Blood spiked Enriched $10^7$ | 37.95 | |

TABLE 11.4b

Phage DNA qPCR results for spiked blood with and without viral enrichment.

| Sample ID | Phage qPCR assay (Cq) | Average ΔCq against PC |
|---|---|---|
| PC blood spiked $10^4$ | 31.10 | 2.36 |
| Blood spiked Enriched $10^4$ | 33.46 | |
| PC blood spiked $10^5$ | 28.14 | 0.65 |
| Blood spiked Enriched $10^5$ | 28.79 | |
| PC blood spiked $10^6$ | 23.96 | 0.34 |
| Blood spiked Enriched $10^6$ | 24.30 | |
| PC blood spiked $10^7$ | 20.66 | 0.07 |
| Blood spiked Enriched $10^7$ | 20.73 | |

Conclusion:

Here we described a complete protocol for the depletion of host DNA and enrichment of viral (both DNA and RNA) and phage (DNA). Two methods have been developed (one working in plasma; section 11.1, and one working in blood; section 11.2), and both provide human DNA depletion (~$10^4$ fold depletion in blood to undetectable in plasma). There is no loss of viral and phage DNA targets or viral HIV RNA target.

Example 12—Altering the Cytolysin (Blood Samples)

For all testing with other cytolysins, 200 µl of blood was used following the protocol set out in section 10.2. The only alteration was the addition of different volumes/concentrations in place of PLC, i.e. no optimization was carried out.

Phospholipase D (PLD) from *Streptomyces*

PLD was purchased from Sigma-Aldrich® (P0065-25KU) with a stock made to 50KU/ml; varying volumes of PLD were used (2, 5 and 8 µl). Human DNA was depleted <$10^2$ fold (Table 12.1a) with no loss of bacterial or fungal targets (Tables 12.1b,c,d).

TABLE 12.1a

Human DNA qPCR results for spiked blood with and without bacterial/fungal enrichment using PLD.

| Sample ID | Human qPCR assay (Cq) | Average ΔCq against PC |
|---|---|---|
| PC blood 1 Unenriched | 23.07 | 3.68 |
| Blood 1 Enriched 2 µl | 26.75 | |
| PC blood 2 Unenriched | 23.05 | 5.76 |
| Blood 2 Enriched 5 µl | 28.81 | |
| PC blood 3 Unenriched | 23.28 | 3.76 |
| Blood 3 Enriched 8 µl | 27.04 | |

TABLE 12.1b

*E. coli* DNA qPCR results for spiked blood with and without bacterial/fungal enrichment using PLD.

| Sample ID | *E. coli* qPCR assay (Cq) | Average ΔCq against PC |
|---|---|---|
| PC blood 1 Unenriched | 25.98 | 1.02 |
| Blood 1 Enriched 2 µl | 24.96 | |
| PC blood 2 Unenriched | 25.29 | 0.2 |
| Blood 2 Enriched 5 µl | 25.09 | |
| PC blood 3 Unenriched | 27.32 | 0.55 |
| Blood 3 Enriched 8 µl | 26.77 | |

TABLE 12.1c

*S. aureus* DNA qPCR results for spiked blood with and without bacterial/fungal enrichment using PLD.

| Sample ID | *S aureus* qPCR assay (Cq) | Average ΔCq against PC |
|---|---|---|
| PC blood 1 Unenriched | 24.01 | 0.69 |
| Blood 1 Enriched 2 µl | 23.32 | |
| PC blood 2 Unenriched | 23.20 | 0.78 |
| Blood 2 Enriched 5 µl | 23.98 | |
| PC blood 3 Unenriched | 23.06 | 0.33 |
| Blood 3 Enriched 8 µl | 22.73 | |

TABLE 12.1d

C. albicans DNA qPCR results for spiked blood with and without bacterial/fungal enrichment using PLD.

| Sample ID | C albicans qPCR assay (Cq) | Average ΔCq against PC |
|---|---|---|
| PC blood 1 Unenriched | 29.55 | 0.53 |
| Blood 1 Enriched 2 µl | 29.02 | |
| PC blood 2 Unenriched | 29.58 | 0.35 |
| Blood 2 Enriched 5 µl | 29.93 | |
| PC blood 3 Unenriched | 29.91 | 0.15 |
| Blood 3 Enriched 8 µl | 29.76 | |

**Sphingomyelinase from *S. aureus***

Sphingomyelinase was purchased from Sigma-Aldrich® (58633-25UN) in solution and varying volumes were used (2, 5 and 8 µl). Human DNA was depleted <$10^2$ fold (Table 12.2a) with no loss of bacterial or fungal targets (Tables 12.2b,c,d).

TABLE 12.2a

Human DNA qPCR results for spiked blood with and without bacterial/fungal enrichment using sphingomyelinase.

| Sample ID | Human qPCR assay (Cq) | Average ΔCq against PC |
|---|---|---|
| PC blood 1 Unenriched | 23.07 | 4.57 |
| Blood 1 Enriched 2 µl | 27.64 | |
| PC blood 2 Unenriched | 23.05 | 7.53 |
| Blood 2 Enriched 5 µl | 30.58 | |
| PC blood 3 Unenriched | 23.28 | 5.46 |
| Blood 3 Enriched 8 µl | 28.74 | |

TABLE 12.2b

E. coli DNA qPCR results for spiked blood with and without bacterial/fungal enrichment using sphingomyelinase.

| Sample ID | E. coli qPCR assay (Cq) | Average ΔCq against PC |
|---|---|---|
| PC blood 1 Unenriched | 25.98 | 1.61 |
| Blood 1 Enriched 2 µl | 24.67 | |
| PC blood 2 Unenriched | 25.29 | 0.03 |
| Blood 2 Enriched 5 µl | 25.26 | |
| PC blood 3 Unenriched | 27.32 | 0.65 |
| Blood 3 Enriched 8 µl | 26.67 | |

TABLE 12.2c

S. aureus DNA qPCR results for spiked blood with and without bacterial/fungal enrichment using sphingomyelinase.

| Sample ID | S aureus qPCR assay (Cq) | Average ΔCq against PC |
|---|---|---|
| PC blood 1 Unenriched | 24.01 | 1.36 |
| Blood 1 Enriched 2 µl | 22.65 | |
| PC blood 2 Unenriched | 23.20 | 0.92 |
| Blood 2 Enriched 5 µl | 24.12 | |
| PC blood 3 Unenriched | 23.06 | 0.73 |
| Blood 3 Enriched 8 µl | 22.66 | |

TABLE 12.2d

C. albicans DNA qPCR results for spiked blood with and without bacterial/fungal enrichment using sphingomyelinase.

| Sample ID | C albicans qPCR assay (Cq) | Average ΔCq against PC |
|---|---|---|
| PC blood 1 Unenriched | 29.55 | 1.73 |
| Blood 1 Enriched 2 µl | 27.82 | |
| PC blood 2 Unenriched | 29.58 | 0.11 |
| Blood 2 Enriched 5 µl | 29.69 | |
| PC blood 3 Unenriched | 29.91 | 0.92 |
| Blood 3 Enriched 8 µl | 28.99 | |

**Alpha Hemolysin from *S. aureus***

Alpha hemolysin was purchased from Sigma-Aldrich® (H9395-5MG) and added at 0.01, 0.08 or 0.8 mg in 20 µl water. Human DNA was depleted <$10^2$ fold (Table 12.3a) with no loss of bacterial or fungal targets (Tables 12.3b,c,d).

TABLE 12.3a

Human DNA qPCR results for spiked blood with and without bacterial/fungal enrichment using alpha hemolysin.

| Sample ID | Human qPCR assay (Cq) | Average ΔCq against PC |
|---|---|---|
| PC blood 1 Unenriched | 23.06 | 1.45 |
| Blood 1 Enriched 0.01 mg | 24.48 | |
| PC blood 2 Unenriched | 23.28 | 4.38 |
| Blood 2 Enriched 0.08 mg | 27.63 | |
| PC blood 3 Unenriched | 23.28 | 3.94 |
| Blood 3 Enriched 0.8 mg | 27.22 | |

TABLE 12.3b

E. coli DNA qPCR results for spiked blood with and without bacterial/fungal enrichment using alpha hemolysin.

| Sample ID | E. coli qPCR assay (Cq) | Average ΔCq against PC |
|---|---|---|
| PC blood 1 Unenriched | 26.96 | 0.59 |
| Blood 1 Enriched 0.01 mg | 26.37 | |
| PC blood 2 Unenriched | 27.32 | 0.11 |
| Blood 2 Enriched 0.08 mg | 27.21 | |
| PC blood 3 Unenriched | 27.32 | 0.02 |
| Blood 3 Enriched 0.8 mg | 27.34 | |

TABLE 12.3c

S. aureus DNA qPCR results for spiked blood with and without bacterial/fungal enrichment using alpha hemolysin.

| Sample ID | S aureus qPCR assay (Cq) | Average ΔCq against PC |
|---|---|---|
| PC blood 1 Unenriched | 22.71 | 0.41 |
| Blood 1 Enriched 0.01 mg | 23.12 | |
| PC blood 2 Unenriched | 23.06 | 0.3 |
| Blood 2 Enriched 0.08 mg | 22.73 | |
| PC blood 3 Unenriched | 23.06 | 0.06 |
| Blood 3 Enriched 0.8 mg | 23.12 | |

TABLE 12.3d

C. albicans DNA qPCR results for spiked blood with and without bacterial/fungal enrichment using alpha hemolysin.

| Sample ID | C albicans qPCR assay (Cq) | Average ΔCq against PC |
|---|---|---|
| PC blood 1 Unenriched | 28.57 | 0.41 |
| Blood 1 Enriched 0.01 mg | 28.16 | |
| PC blood 2 Unenriched | 29.91 | 1.75 |
| Blood 2 Enriched 0.08 mg | 28.16 | |
| PC blood 3 Unenriched | 29.91 | 0.1 |
| Blood 3 Enriched 0.8 mg | 29.81 | |

Streptolysin O from *S. pyogenes*

Streptolysin O was purchased from Sigma-Aldrich® (55265-25KU) and added at 0.08 or 0.8 mg in 20 μl water. Human DNA was depleted 10 fold (Table 12.4a) with no loss of bacterial or fungal targets (Tables 12.4b,c,d).

TABLE 12.4a

Human DNA qPCR results for spiked blood with and without bacterial/fungal enrichment using streptolysin O.

| Sample ID | Human qPCR assay (Cq) | Average ΔCq against PC |
|---|---|---|
| PC blood 1 Unenriched | 23.28 | 2.87 |
| Blood 1 Enriched 0.08 mg | 26.15 | |
| PC blood 2 Unenriched | 23.28 | 2.9 |
| Blood 2 Enriched 0.8 mg | 26.18 | |

TABLE 12.4b

E. coli DNA qPCR results for spiked blood with and without bacterial/fungal enrichment using streptolysin O.

| Sample ID | E. coli qPCR assay (Cq) | Average ΔCq against PC |
|---|---|---|
| PC blood 1 Unenriched | 27.32 | 0.08 |
| Blood 1 Enriched 0.08 mg | 27.24 | |
| PC blood 2 Unenriched | 27.32 | 0.32 |
| Blood 2 Enriched 0.8 mg | 27.00 | |

TABLE 12.4c

S. aureus DNA qPCR results for spiked blood with and without bacterial/fungal enrichment using streptolysin O.

| Sample ID | S aureus qPCR assay (Cq) | Average ΔCq against PC |
|---|---|---|
| PC blood 1 Unenriched | 23.06 | 0.38 |
| Blood 1 Enriched 0.08 mg | 22.68 | |
| PC blood 2 Unenriched | 23.06 | 0.28 |
| Blood 2 Enriched 0.8 mg | 22.78 | |

TABLE 12.4d

C. albicans DNA qPCR results for spiked blood with and without bacterial/fungal enrichment using streptolysin O.

| Sample ID | C albicans qPCR assay (Cq) | Average ΔCq against PC |
|---|---|---|
| PC blood 1 Unenriched | 29.91 | 0.11 |
| Blood 1 Enriched 0.08 mg | 29.80 | |
| PC blood 2 Unenriched | 29.91 | 1.66 |
| Blood 2 Enriched 0.8 mg | 28.25 | |

Conclusion:

All cytolysins tested showed effective human DNA depletion and no bacterial or fungal DNA loss.

Example 13—Verification of Methodology for Other Clinical Sample Types

Using the established protocol detailed in section 10.2, the initial 200 µl of blood was replaced with 200 µl of sputum, sonicated tissue or urine to verify the depletion method works effectively in other clinical sample types.

Clinical Sputum Samples

Human DNA was depleted up to $10^4$ fold (Table 13.1a) with no loss of bacteria (Tables 13.1b/c) in clinical sputum samples.

TABLE 13.1a

Human DNA qPCR results for clinical sputum with and without fungal/bacterial enrichment.

| Sample ID | Human qPCR assay (Cq) | Average ΔCq against PC |
|---|---|---|
| PC sputum 1 Unenriched | 19.81 | 8.08 |
| Sputum 1 Enriched | 27.89 | |
| PC sputum 2 Unenriched | 22.10 | 12.31 |
| Sputum 2 Enriched | 34.41 | |

TABLE 13.1b 16S rRNA gene fragment (V3-V4) qPCR results for clinical sputum with and without fungal/bacterial enrichment.

| Sample ID | 16S rRNA qPCR assay (Cq) | Average ΔCq against PC |
|---|---|---|
| PC sputum 1 Unenriched | 17.96 | 3.97 |
| Sputum 1 Enriched | 13.93 | |
| PC sputum 2 Unenriched | 15.89 | 0.23 |
| Sputum 2 Enriched | 15.66 | |

TABLE 13.1c

S. aureus DNA qPCR results for clinical sputum with and without fungal/bacterial enrichment.

| Sample ID | S aureus qPCR assay (Cq) | Average ΔCq against PC |
|---|---|---|
| PC sputum 2 Unenriched (suspected S aureus) | 22.29 | 0.87 |
| Sputum 2 Enriched (suspected S aureus) | 22.96 | |

Peri Prosthetic Tissue Samples

Peri-prosthetic tissue sample biopsies spiked with *Staphylococcus epidermidis* cells (15TB0821), with <$10^5$ fold human DNA depletion (Table 13.2a) and no loss of bacterial target (Table 13.2b).

TABLE 13.2a

Human DNA qPCR results for per-prosthetic spiked tissue samples with and without fungal/bacterial enrichment.

| Sample ID | Human qPCR assay (Cq) | ΔCq against PC |
|---|---|---|
| PC tissue Unenriched | 23.09 | |
| Tissue 100 cells Enriched | 37.87 | 14.78 |
| Tissue 1000 cells Enriched | 37.90 | 14.81 |
| Tissue 10,000 cells Enriched | 38.37 | 15.28 |

TABLE 13.2b

*S. epidermidis* DNA qPCR results for peri-prosthetic spiked tissue samples with and without fungal/bacterial enrichment.

| Sample ID | S epidermidis qPCR assay (Cq) | ΔCq against PC |
|---|---|---|
| PC tissue 100 cells Unenriched | 37.25 | 1.99 |
| Tissue 100 cells Enriched | 35.26 | |

Clinical Urine Samples

Human DNA was depleted <$10^4$ fold (Table 13.3a) with no loss of bacteria (Tables 13.3b/c) in clinical sputum samples.

TABLE 13.3a

Human DNA qPCR results for clinical urine with and without fungal/bacterial enrichment.

| Sample ID | Human qPCR assay (Cq) | Average ΔCq against PC |
|---|---|---|
| PC urine 1 Unenriched | 24.01 | 10.99 |
| Urine 1 Enriched | 35 | |
| PC urine 2 Unenriched | 31.26 | 3.74 |
| Urine 2 Enriched | 35 | |
| PC urine 3 Unenriched | 24.98 | 10.32 |
| Urine 3 Enriched | 35 | |

TABLE 13.3b 16S rRNA gene fragment (V3-V4) qPCR results for clinical urine with and without fungal/bacterial enrichment.

| Sample ID | 16S rRNA qPCR assay (Cq) | Average ΔCq against PC |
|---|---|---|
| PC urine 1 Unenriched | 13.60 | 0.32 |
| Urine 1 Enriched | 13.92 | |
| PC urine 2 Unenriched | 14.16 | 1.34 |
| Urine 2 Enriched | 15.50 | |

TABLE 13.3b-continued 16S rRNA gene fragment (V3-V4) qPCR results for clinical urine with and without fungal/bacterial enrichment.

| Sample ID | 16S rRNA qPCR assay (Cq) | Average ΔCq against PC |
|---|---|---|
| PC urine 3 Unenriched | 10.90 | 0.36 |
| Urine 3 Enriched | 10.54 | |

TABLE 13.3c

E. coli DNA qPCR results for clinical urine with and without fungal/bacterial enrichment.

| Sample ID | E coli qPCR assay (Cq) | Average ΔCq against PC |
|---|---|---|
| PC urine 2 Unenriched (suspected E. coli) | 19.46 | 1.27 |
| Urine 2 Enriched (suspected E. coli) | 20.73 | |

Conclusion: All clinical sample types tested showed host DNA depletion with no loss of bacterial DNA.

Example 14—Host RNA Depletion (HL-SAN RNase Activity)

There was >10² fold host RNA depletion using the viral blood protocol (section 11.2 and Table 14.1a). Using the viral plasma protocol detailed in section 11.1, showed >10² fold depletion of host RNA (Table 14.1b and 14.2a) with no loss of HIV target (Table 14.2b).

TABLE 14.1a

Human RNA RT-qPCR results in duplicate for non-spiked blood with and without viral enrichment (host RNA depletion).

| Sample ID | Human RNA qPCR assay (Cq) | Average ΔCq against PC |
|---|---|---|
| Unenriched blood non-spiked 1 | 24.72 | 8.53 |
| Enriched blood non-spiked 1 | 33.25 | |
| Unenriched blood non-spiked 2 | 32.49 | 5.9 |
| Enriched blood non-spiked 2 | 38.39 | |

TABLE 14.1b

Human RNA RT-qPCR results in duplicate for non-spiked plasma with and without viral enrichment (host RNA depletion).

| Sample ID | Human RNA qPCR assay (Cq) | Average ΔCq against PC |
|---|---|---|
| Unenriched plasma unspiked 1 | 36.26 | 8.74 |
| Enriched plasma Unspiked 1 | Undetectable | |
| Unenriched plasma unspiked 2 | 34.44 | 10.56 |
| Enriched plasma Unspiked 2 | Undetectable | |

TABLE 14.2a

Human RNA RT-qPCR results in duplicate for spiked plasma with and without viral enrichment (host RNA depletion).

| Sample ID | Human RNA qPCR assay (Cq) | Average ΔCq against PC |
|---|---|---|
| Unenriched plasma spiked 1 | 36.35 | 8.65 |
| Enriched plasma spiked 1 | Undetectable | |
| Unenriched plasma spiked 2 | 30.87 | 3.28 |
| Enriched plasma spiked 2 | 34.15 | |

TABLE 14.2b

HIV RNA RT-qPCR results in duplicate for spiked plasma with and without viral enrichment (host RNA depletion).

| Sample ID | HIV RNA qPCR assay (Cq) | Average ΔCq against PC |
|---|---|---|
| Unenriched plasma spiked 1 | 35.67 | 0.36 |
| Enriched plasma spiked 1 | 36.03 | |
| Unenriched plasma spiked 2 | 31.95 | 0.78 |
| Enriched plasma spiked 2 | 32.73 | |

Conclusion:

Due to the variability of starting host RNA, it was established that HL-SAN RNase activity provided the greatest host RNA depletion with no loss of viral RNA target and therefore no alterations to the enrichment protocol (detailed in section 11.1) was necessary. Human RNA was typically not detectable in plasma post depletion using this method.

Example 15—Removal of Human DNA without Nuclease

Propidium Monoazide (PMA) to Remove Human DNA

An altered method from that described in section 10.2 was needed to enable the activation of PMA by light. After PLC treatment, the sample was centrifuged at 12,000×g for 5 min and resuspended in 1.5 ml of PBS. PMA was added at a final concentration of 5004 and incubated in the dark with occasional shaking for 5 min. The sample was then placed in a photolysis device for 15 min exposure to blue light, the protocol in section 10.2 was then followed from step 6. Human DNA was depleted <10² fold (Table 15.1) with no loss of bacterial target DNA (Table 15.2).

TABLE 15.1

Human DNA qPCR results for spiked blood samples with and without fungal/bacterial enrichment using PMA to remove human DNA.

| Sample ID | Human qPCR assay (Cq) | ΔCq against PC |
|---|---|---|
| PC blood Unenriched | 22.90 | |
| Blood PMA #1 Enriched | 27.62 | 4.72 |
| Blood PMA #2 Enriched | 28.47 | 5.57 |

TABLE 15.2

*E. coli* DNA qPCR results for spiked blood samples with and without fungal/bacterial enrichment using PMA to remove human DNA.

| Sample ID | *E. coli* qPCR assay (Cq) | ΔCq against PC |
|---|---|---|
| PC blood Unenriched | 20.65 | |
| Blood PMA #1 Enriched | 21.13 | 0.48 |
| Blood PMA #2 Enriched | 21.30 | 0.65 |

Conclusion:

Using PMA to remove human DNA after PLC treatment showed human DNA depletion and no loss of bacterial target DNA

Example 16—Revised Protocol for 1 ml Blood Sample

1. PLC was added (4 mg/100 µl) to the blood sample (1 ml in a 5 ml bijou tube), vortexed and incubated at 37° C. for 3 min in a water bath followed by 38° C. for 20 min with slow mixing at 15 rpm in a Hulamixer®.
2. Sample was transferred to a 2 ml tube and 500 µl of HL-SAN buffer (5M NaCl and 100 mM $MgCl_2$) was added and incubated 37° C. for 15 min in a heatblock at 1000 RPM.
3. Cells were pelleted by centrifugation at 8,000×g for 5 min.
4. The cell pellet was resuspended in 200 µl PBS
5. HL-SAN buffer was added at a 1:1 volume ratio (200 µl) with 10 µl HL-SAN DNase, vortexed and incubated at 37° C. for 15 min at 1000 RPM in a heat block.
6. PBS was added to a total volume of 2 ml (1.5 ml).
7. Cells were pelleted by centrifugation at 12,000×g for 10 min and the supernatant was discarded.
8. The cell pellet was resuspended in 1.5 ml PBS.
9. Cells were pelleted again by centrifugation at 12,000×g for 10 min and the supernatant was discarded.
10. To any test samples; 350 µl bacterial lysis buffer, 20 µl enzyme cocktail (6 µl mutanolysin 25 ku/ml, 5 µl lysozyme 10 mg/ml, 4 µl lyticase 10 ku/ml, 3 µl lysostaphin 4 ku/ml, 2 µl chitinase 50 u/ml) and 5 µl RNase A was added.
11. All samples were incubated at 37° C. for 15 min at 1000 RPM in a heat block.
12. To all samples, 20 µl proteinase K was added and incubated at 65° C. for 10 min in a heat block.
13. Total nucleic acid was extracted using the MagnaPure® Compact automated machine using the DNA_bacteria_V3_2 protocol.

Changes to the 200 µl protocol in section 10.2 to increase the starting volume to 1 ml are described above. This gave >$10^6$ fold depletion of human DNA (Table 16.1a) with no loss of bacterial or fungal target DNA (Tables 16.1b,c,d).

TABLE 16.1a

Human DNA qPCR results for 1 ml spiked blood with and without fungal/bacterial enrichment.

| Sample ID | Human qPCR assay (Cq) | ΔCq against PC |
|---|---|---|
| PC blood Unenriched | 23.21 | 21.79 |
| Blood 1 ml Enriched | — | |

TABLE 16.1b

*E. coli* DNA qPCR results for 1 ml spiked blood with and without fungal/bacterial enrichment.

| Sample ID | *E coli* qPCR assay (Cq) | ΔCq against PC |
|---|---|---|
| PC blood Unenriched | 31.77 | 2.1 |
| Blood 1 ml Enriched | 29.67 | |

TABLE 16.1c

*S. aureus* DNA qPCR results for 1 ml spiked blood with and without fungal/bacterial enrichment.

| Sample ID | *S aureus* qPCR assay (Cq) | ΔCq against PC |
|---|---|---|
| PC blood Unenriched | 37.63 | 3.72 |
| Blood 1 ml Enriched | 33.91 | |

TABLE 16.1d

*C. albicans* DNA qPCR results for 1 ml spiked blood with and without fungal/bacterial enrichment.

| Sample ID | *C albicans* qPCR assay (Cq) | ΔCq against PC |
|---|---|---|
| PC blood Unenriched | 32.84 | 2.6 |
| Blood 1 ml Enriched | 30.24 | |

Conclusion:

A slightly altered method was developed to enable fungal enrichment when using 1 ml blood and this resulted in ~$10^6$ fold depletion of human DNA with no loss of bacteria or fungi target DNA. Greater sample volumes (>1 ml) could also be used.

This method can seemingly be used on any sample type where the host cells have a phospholipid membrane e.g. clinical samples (infectious disease diagnosis) or animal samples (food safety and veterinary medicine/diagnosis).

Example 17—NGS after Depletion Method

Additional Methodology

After the depletion protocol detailed in section 10.2, 4 µl DNA was processed using REPLI-g single cell kit (Qiagen 150343) for whole genome amplification (WGA). The manufacturer's instructions were followed with the amplification time reduced to 1 hr 30 min. WGA sample (17 µl) was debranched using T7 endonuclease I (NEB M0302S)

according to the manufacturer's instructions. MinION library preparation used the rapid low input by PCR barcoding kit (ONT SQK-RLB001) as per the manufacturer's guideline with the following alterations:

2.5 μl FRM with 7.5 μl template DNA (~140 ng)

40 μl nuclease-free water, 50 μl LongAmp Taq 2×, 2 μl RLB

PCR: [95° C. 3 min]×1, [95° C. 15s, 56° C. 15s, 65° C. 4 min]×20, [65° C. 4 min]×20, [65° C. 6 min]×1

The SpotON R9.4 MinION flowcell was prepared and loaded according to the manufacturer's instructions.

Bioinformatics data analysis: reads were aligned to the *C. albicans* reference genome (SC5314 NC 003977.2) using minimap2. Genome coverage and number of aligned reads were identified using samtools and qualimap. Percentage reads are given as those which aligned to the reference genome out of the total number of reads.

Results

~300 cfu/ml *Candida albicans* at ~15 Mb genome=4.5 pg of DNA

Average concentration of human DNA in 1 ml blood=33 μg of DNA

Therefore before enrichment the ratio of human:*Candida* DNA is ~$10^7$:1

From the sequencing data presented below, *C. albicans* reads are 1% of the total (1.3× genome coverage) therefore assuming all other reads are human=100:1 (human: *Candida*)

Ratio of human:*Candida* DNA before depletion=$10^7$:1
Ratio of human:*Candida* DNA after depletion=100:1
This is the equivalent of $10^5$ fold depletion.

TABLE 17

*C. albicans* genome alignment from single-plex MinION run (input~300 cfu/ml).

| Sequencing time | Total number of reads | Aligned reads to known pathogen | Pathogen genome coverage | Percentage of known pathogen reads (%) |
|---|---|---|---|---|
| 14 hrs | 1.2 million | 12,422 | 1.3 | 1 |

Figure 10:
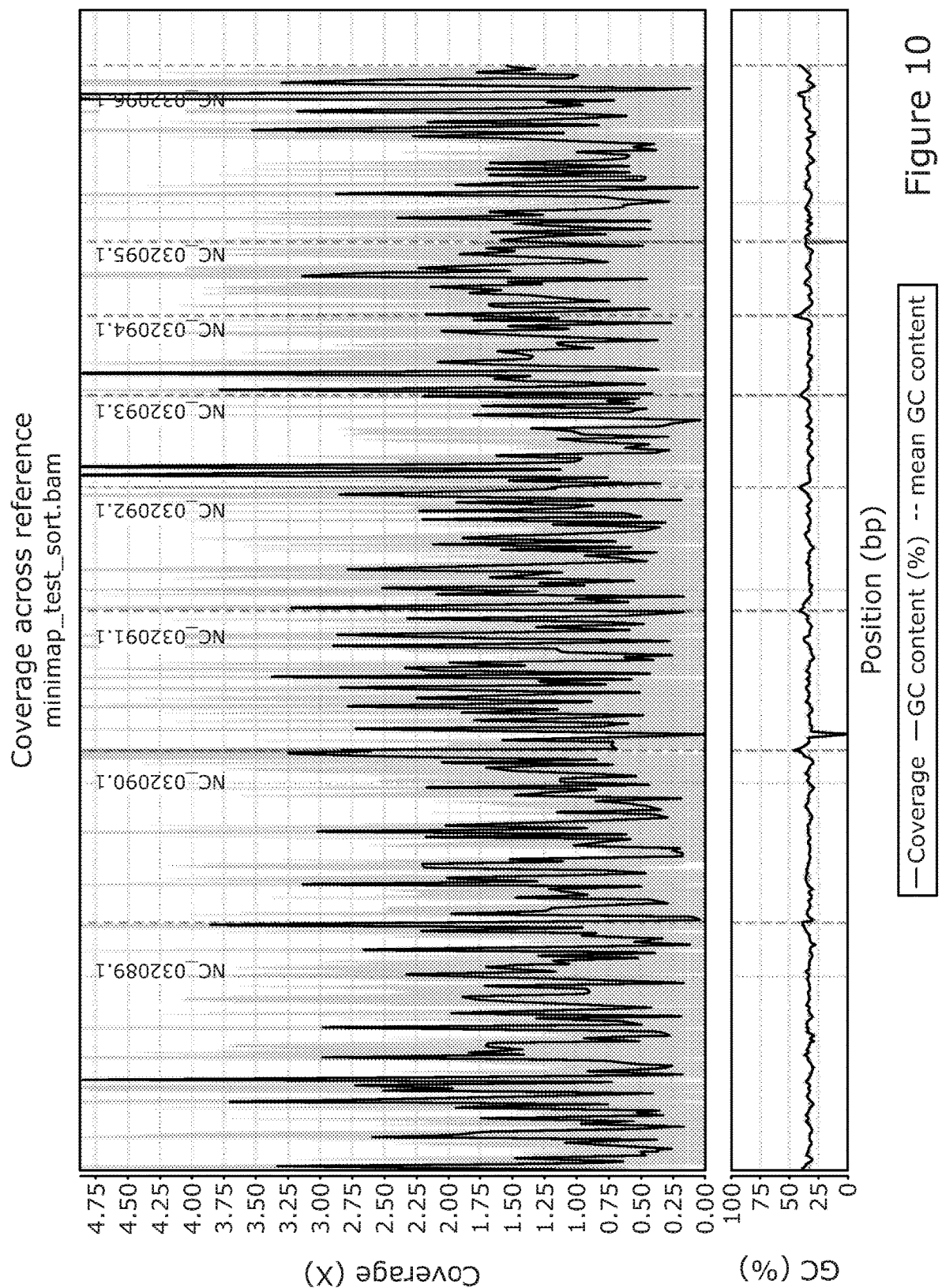
FIG. 10 shows *C. albicans* genome coverage plot after *C. albicans* single-plex MinION sequencing.

*C. albicans* genome coverage plot after *C. albicans* single-plex MinION sequencing is shown in FIG. 10.

The invention claimed is:

1. A method for depleting host nucleic acid in a biological sample while maintaining non-host nucleic acid, said sample having been previously obtained from an animal host, said method comprising the steps of:
(a) adding a phospholipase C, or an active variant thereof, to said sample to selectively lyse host cells in said biological sample; and
(b) carrying-out a process to physically deplete the host nucleic acid released from the lysed host cells within said biological sample, wherein the active variant is a variant of a wild-type phospholipase C that has at least 10% of the lytic activity of the wild-type phospholipase C.

2. The method according to claim 1, wherein step (b) comprises adding a nuclease to said sample.

3. The method according to claim 1, further comprising the step of extracting non-host nucleic acid from the sample.

4. The method according to claim 3, further comprising the step of subjecting the extracted nucleic acid to a purification process.

5. The method according to claim 3, further comprising the step of amplifying the extracted nucleic acid.

6. The method according to claim 3, further comprising the step of conducting a nucleic acid amplification test on the extracted nucleic acid or conducting a sequencing process on the extracted nucleic acid.

7. The method according to claim 1, wherein the PLC is a bacterial PLC.

8. The method according to claim 7, wherein the bacterial PLC is a Group 1 PLC.

9. The method according to claim 8, wherein the Group 1 PLC is PLC from *Clostridium perfringens*.

10. The method according to claim 1, wherein the biological sample is a blood sample.

11. The method according to claim 1, that results in at least a 10 fold depletion of host DNA originally contained within the sample.

12. The method according to claim 1, that results in at least a $10^2$ fold depletion of host DNA originally contained within the sample.

13. The method according to claim 1, that results in at least a $10^3$ fold depletion of host DNA originally contained within the sample.

14. The method according to claim 1, that results in at least a $10^4$ fold depletion of host DNA originally contained within the sample.

15. The method according to claim 1, that results in at least a $10^5$ fold depletion of host DNA originally contained within the sample.

\* \* \* \* \*

SEQUENCE LISTING

```
<160> NUMBER OF SEQ ID NOS: 5

<210> SEQ ID NO 1
<211> LENGTH: 398
<212> TYPE: PRT
<213> ORGANISM: Clostridium perfringens

<400> SEQUENCE: 1

Met Lys Arg Lys Ile Cys Lys Ala Leu Ile Cys Ala Ala Leu Ala Thr
1               5                   10                  15

Ser Leu Trp Ala Gly Ala Ser Thr Lys Val Tyr Ala Trp Asp Gly Lys
            20                  25                  30

Ile Asp Gly Thr Gly Thr His Ala Met Ile Val Thr Gln Gly Val Ser
        35                  40                  45

Ile Leu Glu Asn Asp Met Ser Lys Asn Glu Pro Glu Ser Val Arg Lys
    50                  55                  60

Asn Leu Glu Ile Leu Lys Glu Asn Met His Glu Leu Gln Leu Gly Ser
65                  70                  75                  80

Thr Tyr Pro Asp Tyr Asp Lys Asn Ala Tyr Asp Leu Tyr Gln Asp His
                85                  90                  95

Phe Trp Asp Pro Asp Thr Asp Asn Asn Phe Ser Lys Asp Asn Ser Trp
            100                 105                 110

Tyr Leu Ala Tyr Ser Ile Pro Asp Thr Gly Glu Ser Gln Ile Arg Lys
        115                 120                 125

Phe Ser Ala Leu Ala Arg Tyr Glu Trp Gln Arg Gly Asn Tyr Lys Gln
    130                 135                 140

Ala Thr Phe Tyr Leu Gly Glu Ala Met His Tyr Phe Gly Asp Ile Asp
145                 150                 155                 160

Thr Pro Tyr His Pro Ala Asn Val Thr Ala Val Asp Ser Ala Gly His
                165                 170                 175

Val Lys Phe Glu Thr Phe Ala Glu Glu Arg Lys Glu Gln Tyr Lys Ile
            180                 185                 190

Asn Thr Ala Gly Cys Lys Thr Asn Glu Asp Phe Tyr Ala Asp Ile Leu
        195                 200                 205

Lys Asn Lys Asp Phe Asn Ala Trp Ser Lys Glu Tyr Ala Arg Gly Phe
```

```
            210                 215                 220
Ala Lys Thr Gly Lys Ser Ile Tyr Tyr Ser His Ala Ser Met Ser His
225                 230                 235                 240

Ser Trp Asp Asp Trp Asp Tyr Ala Ala Lys Val Thr Leu Ala Asn Ser
                245                 250                 255

Gln Lys Gly Thr Ala Gly Tyr Ile Tyr Arg Phe Leu His Asp Val Ser
                260                 265                 270

Glu Gly Asn Asp Pro Ser Val Gly Lys Asn Val Lys Glu Leu Val Ala
                275                 280                 285

Tyr Ile Ser Thr Ser Gly Glu Lys Asp Ala Gly Thr Asp Asp Tyr Met
            290                 295                 300

Tyr Phe Gly Ile Lys Thr Lys Asp Gly Lys Thr Gln Glu Trp Glu Met
305                 310                 315                 320

Asp Asn Pro Gly Asn Asp Phe Met Thr Gly Ser Lys Asp Thr Tyr Thr
                325                 330                 335

Phe Lys Leu Lys Asp Glu Asn Leu Lys Ile Asp Asp Ile Gln Asn Met
                340                 345                 350

Trp Ile Arg Lys Arg Lys Tyr Thr Ala Phe Pro Asp Ala Tyr Lys Pro
                355                 360                 365

Glu Asn Ile Lys Val Ile Ala Asn Gly Lys Val Val Asp Lys Asp
            370                 375                 380

Ile Asn Glu Trp Ile Ser Gly Asn Ser Thr Tyr Asn Ile Lys
385                 390                 395

<210> SEQ ID NO 2
<211> LENGTH: 319
<212> TYPE: PRT
<213> ORGANISM: Staphylococcus aureus

<400> SEQUENCE: 2

Met Lys Thr Arg Ile Val Ser Ser Val Thr Thr Thr Leu Leu Leu Gly
1               5                   10                  15

Cys Ile Leu Met Asn Pro Val Ala Asn Ala Ala Asp Ser Asp Ile Asn
                20                  25                  30

Ile Lys Thr Gly Thr Thr Asp Ile Gly Ser Asn Thr Thr Val Lys Thr
            35                  40                  45

Gly Asp Leu Val Thr Tyr Asp Lys Glu Asn Gly Met His Lys Lys Val
        50                  55                  60

Phe Tyr Ser Phe Ile Asp Asp Lys Asn His Asn Lys Lys Ile Leu Val
65                  70                  75                  80

Ile Arg Thr Lys Gly Thr Ile Ala Gly Gln Tyr Arg Val Tyr Ser Glu
                85                  90                  95

Glu Gly Ala Asn Lys Ser Gly Leu Ala Trp Pro Ser Ala Phe Lys Val
                100                 105                 110

Gln Leu Gln Leu Pro Asp Asn Glu Val Ala Gln Ile Ser Asp Tyr Tyr
            115                 120                 125

Pro Arg Asn Ser Ile Asp Thr Lys Glu Tyr Met Ser Thr Leu Thr Tyr
        130                 135                 140

Gly Phe Asn Gly Asn Val Thr Gly Asp Asp Ser Gly Lys Ile Gly Gly
145                 150                 155                 160

Leu Ile Gly Ala Asn Val Ser Ile Gly His Thr Leu Lys Tyr Val Gln
                165                 170                 175

Pro Asp Phe Lys Thr Ile Leu Glu Ser Pro Thr Asp Lys Lys Val Gly
                180                 185                 190
```

```
Trp Lys Val Ile Phe Asn Asn Met Val Asn Gln Asn Trp Gly Pro Tyr
            195                 200                 205

Asp Arg Asp Ser Trp Asn Pro Val Tyr Gly Asn Gln Leu Phe Met Lys
210                 215                 220

Thr Arg Asn Gly Ser Met Lys Ala Ala Asp Asn Phe Leu Asp Pro Asn
225                 230                 235                 240

Lys Ala Ser Ser Leu Leu Ser Ser Gly Phe Ser Pro Asp Phe Ala Thr
                245                 250                 255

Val Ile Thr Met Asp Arg Lys Ala Ser Lys Gln Gln Thr Asn Ile Asp
                260                 265                 270

Val Ile Tyr Glu Arg Val Arg Asp Asp Tyr Gln Leu Tyr Trp Thr Ser
                275                 280                 285

Thr Asn Trp Lys Gly Thr Asn Thr Lys Asp Lys Trp Thr Asp Arg Ser
            290                 295                 300

Ser Glu Arg Tyr Lys Ile Asp Trp Glu Lys Glu Met Thr Asn
305                 310                 315

<210> SEQ ID NO 3
<211> LENGTH: 571
<212> TYPE: PRT
<213> ORGANISM: Streptococcus pyogenes

<400> SEQUENCE: 3

Met Ser Asn Lys Lys Thr Phe Lys Lys Tyr Ser Arg Val Ala Gly Leu
1               5                   10                  15

Leu Thr Ala Ala Leu Ile Ile Gly Asn Leu Val Thr Ala Asn Ala Glu
                20                  25                  30

Ser Asn Lys Gln Asn Thr Ala Ser Thr Glu Thr Thr Thr Ser Glu
            35                  40                  45

Gln Pro Lys Pro Glu Ser Ser Glu Leu Thr Ile Glu Lys Ala Gly Gln
    50                  55                  60

Lys Met Asp Asp Met Leu Asn Ser Asn Asp Met Ile Lys Leu Ala Pro
65                  70                  75                  80

Lys Glu Met Pro Leu Glu Ser Ala Glu Lys Glu Glu Lys Lys Ser Glu
                85                  90                  95

Asp Lys Lys Lys Ser Glu Glu Asp His Thr Glu Glu Ile Asn Asp Lys
                100                 105                 110

Ile Tyr Ser Leu Asn Tyr Asn Glu Leu Glu Val Leu Ala Lys Asn Gly
            115                 120                 125

Glu Thr Ile Glu Asn Phe Val Pro Lys Glu Gly Val Lys Lys Ala Asp
    130                 135                 140

Lys Phe Ile Val Ile Glu Arg Lys Lys Asn Ile Asn Thr Thr Pro
145                 150                 155                 160

Val Asp Ile Ser Ile Ile Asp Ser Val Thr Asp Arg Thr Tyr Pro Ala
                165                 170                 175

Ala Leu Gln Leu Ala Asn Lys Gly Phe Thr Glu Asn Lys Pro Asp Ala
                180                 185                 190

Val Val Thr Lys Arg Asn Pro Gln Lys Ile His Ile Asp Leu Pro Gly
            195                 200                 205

Met Gly Asp Lys Ala Thr Val Glu Val Asn Asp Pro Thr Tyr Ala Asn
    210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
                245                 250                 255
```

```
Val Tyr Ser Lys Ser Gln Ile Glu Ala Ala Leu Asn Val Asn Ser Lys
            260                 265                 270

Ile Leu Asp Gly Thr Leu Gly Ile Asp Phe Lys Ser Ile Ser Lys Gly
        275                 280                 285

Glu Lys Lys Val Met Ile Ala Ala Tyr Lys Gln Ile Phe Tyr Thr Val
    290                 295                 300

Ser Ala Asn Leu Pro Asn Asn Pro Ala Asp Val Phe Asp Lys Ser Val
305                 310                 315                 320

Thr Phe Lys Asp Leu Gln Arg Lys Gly Val Ser Asn Glu Ala Pro Pro
                325                 330                 335

Leu Phe Val Ser Asn Val Ala Tyr Gly Arg Thr Val Phe Val Lys Leu
            340                 345                 350

Glu Thr Ser Ser Lys Ser Asn Asp Val Glu Ala Ala Phe Ser Ala Ala
        355                 360                 365

Leu Lys Gly Thr Asp Val Lys Thr Asn Gly Lys Tyr Ser Asp Ile Leu
    370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
                405                 410                 415

Lys Asp Asn Ala Thr Phe Ser Arg Lys Asn Pro Ala Tyr Pro Ile Ser
            420                 425                 430

Tyr Thr Ser Val Phe Leu Lys Asn Asn Lys Ile Ala Gly Val Asn Asn
        435                 440                 445

Arg Thr Glu Tyr Val Glu Thr Thr Ser Thr Tyr Thr Ser Gly Lys
    450                 455                 460

Ile Asn Leu Ser His Gln Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
                485                 490                 495

Arg Arg Trp Asp Asn Asn Trp Tyr Ser Lys Thr Ser Pro Phe Ser Thr
            500                 505                 510

Val Ile Pro Leu Gly Ala Asn Ser Arg Asn Ile Arg Ile Met Ala Arg
        515                 520                 525

Glu Cys Thr Gly Leu Ala Trp Glu Trp Trp Arg Lys Val Ile Asp Glu
    530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
                565                 570

<210> SEQ ID NO 4
<211> LENGTH: 331
<212> TYPE: PRT
<213> ORGANISM: Staphylococcus aureus

<400> SEQUENCE: 4

Met Met Val Lys Lys Thr Lys Ser Asn Ser Leu Lys Lys Val Ala Thr
1               5                   10                  15

Leu Ala Leu Ala Asn Leu Leu Val Gly Ala Leu Thr Asp Asn Ser
            20                  25                  30

Ala Lys Ala Glu Ser Lys Lys Asp Asp Thr Asp Leu Lys Leu Val Ser
        35                  40                  45

His Asn Val Tyr Met Leu Ser Thr Val Leu Tyr Pro Asn Trp Gly Gln
```

-continued

Tyr Lys Arg Ala Asp Leu Ile Gly Gln Ser Ser Tyr Ile Lys Asn Asn
 65              70                  75                  80

Asp Val Val Ile Phe Asn Glu Ala Phe Asp Asn Gly Ala Ser Asp Lys
                 85                  90                  95

Leu Leu Ser Asn Val Lys Lys Glu Tyr Pro Tyr Gln Thr Pro Val Leu
            100                 105                 110

Gly Arg Ser Gln Ser Gly Trp Asp Lys Thr Glu Gly Tyr Ser Ser
            115                 120                 125

Thr Val Ala Glu Asp Gly Val Ala Ile Val Ser Lys Tyr Pro Ile
        130                 135                 140

Lys Glu Lys Ile Gln His Val Phe Lys Ser Gly Cys Gly Phe Asp Asn
145             150                 155                 160

Asp Ser Asn Lys Gly Phe Val Tyr Thr Lys Ile Glu Lys Asn Gly Lys
                165                 170                 175

Asn Val His Val Ile Gly Thr His Thr Gln Ser Glu Asp Ser Arg Cys
            180                 185                 190

Gly Ala Gly His Asp Arg Lys Ile Arg Ala Glu Gln Met Lys Glu Ile
            195                 200                 205

Ser Asp Phe Val Lys Lys Asn Ile Pro Lys Asp Glu Thr Val Tyr
210             215                 220

Ile Gly Gly Asp Leu Asn Val Asn Lys Gly Thr Pro Glu Phe Lys Asp
225             230                 235                 240

Met Leu Lys Asn Leu Asn Val Asn Asp Val Leu Tyr Ala Gly His Asn
                245                 250                 255

Ser Thr Trp Asp Pro Gln Ser Asn Ser Ile Ala Lys Tyr Asn Tyr Pro
            260                 265                 270

Asn Gly Lys Pro Glu His Leu Asp Tyr Ile Phe Thr Asp Lys Asp His
            275                 280                 285

Lys Gln Pro Lys Gln Leu Val Asn Glu Val Val Thr Glu Lys Pro Lys
290                 295                 300

Pro Trp Asp Val Tyr Ala Phe Pro Tyr Tyr Val Tyr Asn Asp Phe
305             310                 315                 320

Ser Asp His Tyr Pro Ile Lys Ala Tyr Ser Lys
            325                 330

<210> SEQ ID NO 5
<211> LENGTH: 553
<212> TYPE: PRT
<213> ORGANISM: Streptomyces vinaceus

<400> SEQUENCE: 5

Met His Arg His Thr Pro Ser Leu Arg Arg Pro Ser Ala His Leu Pro
1               5                   10                  15

Ser Ala Leu Ala Val Arg Ala Ala Val Pro Ala Ala Leu Leu Ala Leu
            20                  25                  30

Phe Ala Ala Val Pro Ala Ser Ala Ala Pro Ala Ala Gly Ser Gly Ala
        35                  40                  45

Asp Pro Ala Pro His Leu Asp Ala Val Glu Gln Thr Leu Arg Gln Val
    50                  55                  60

Ser Pro Gly Leu Glu Gly Gln Val Trp Glu Arg Thr Ala Gly Asn Val
65              70                  75                  80

Leu Asp Ala Ser Thr Pro Gly Gly Ala Asp Trp Leu Leu Gln Thr Pro
                85                  90                  95

```
Gly Cys Trp Gly Asp Asp Lys Cys Thr Ala Arg Pro Gly Thr Glu Gln
            100                 105                 110

Leu Leu Ser Lys Met Thr Gln Asn Ile Ser Gln Ala Thr Arg Thr Val
            115                 120                 125

Asp Ile Ser Thr Leu Ala Pro Phe Pro Asn Gly Ala Phe Gln Asp Ala
            130                 135                 140

Ile Val Ser Gly Leu Lys Thr Ser Ala Ala Arg Gly Asn Lys Leu Lys
145                 150                 155                 160

Val Arg Val Leu Val Gly Ala Ala Pro Val Tyr His Leu Asn Val Leu
            165                 170                 175

Pro Ser Lys Tyr Arg Asp Glu Leu Val Ala Lys Leu Gly Ala Asp Ala
            180                 185                 190

Arg Asn Val Asp Leu Asn Val Ala Ser Met Thr Thr Ser Lys Thr Ala
            195                 200                 205

Phe Ser Trp Asn His Ser Lys Leu Leu Val Val Asp Gly Gln Ser Val
            210                 215                 220

Ile Thr Gly Gly Ile Asn Asp Trp Lys Asp Asp Tyr Leu Glu Thr Ala
225                 230                 235                 240

His Pro Val Ala Asp Val Asp Leu Ala Leu Arg Gly Pro Ala Ala Ala
            245                 250                 255

Ser Ala Gly Arg Tyr Leu Asp Glu Leu Trp Ser Trp Thr Cys Gln Asn
            260                 265                 270

Lys Ser Asn Ile Ala Ser Val Trp Phe Ala Ser Ser Asn Gly Ala Ala
            275                 280                 285

Cys Met Pro Ala Met Ala Lys Asp Thr Ala Pro Ala Ala Pro Ala Pro
            290                 295                 300

Ala Pro Gly Asp Val Pro Ala Val Ala Val Gly Gly Leu Gly Val Gly
305                 310                 315                 320

Ile Lys Arg Asn Asp Pro Ser Ser Ser Phe Arg Pro Ala Leu Pro Ser
            325                 330                 335

Ala Pro Asp Thr Lys Cys Val Val Gly Leu His Asp Asn Thr Asn Ala
            340                 345                 350

Asp Arg Asp Tyr Asp Thr Val Asn Pro Glu Glu Ser Ala Leu Arg Thr
            355                 360                 365

Leu Ile Ser Ser Ala Asn Arg His Ile Glu Ile Ser Gln Gln Asp Val
            370                 375                 380

Asn Ala Thr Cys Pro Pro Leu Pro Arg Tyr Asp Ile Arg Val Tyr Asp
385                 390                 395                 400

Ala Leu Ala Ala Arg Met Ala Ala Gly Val Lys Val Arg Ile Val Val
            405                 410                 415

Ser Asp Pro Ala Asn Arg Gly Ala Val Gly Ser Gly Gly Tyr Ser Gln
            420                 425                 430

Ile Lys Ser Leu Ser Glu Ile Ser Asp Thr Leu Arg Asp Arg Leu Ala
            435                 440                 445

Leu Val Thr Gly Asp Gln Gly Ala Ala Lys Ala Thr Met Cys Ser Asn
            450                 455                 460

Leu Gln Leu Ala Thr Phe Arg Ser Ser Gln Ser Pro Thr Trp Ala Asp
465                 470                 475                 480

Gly His Pro Tyr Ala Gln His His Lys Val Val Ser Val Asp Asp Ser
            485                 490                 495

Ala Phe Tyr Ile Gly Ser Lys Asn Leu Tyr Pro Ala Trp Leu Gln Asp
            500                 505                 510

Phe Gly Tyr Val Val Glu Ser Pro Ala Ala Ala Ala Gln Leu Asn Ala
```

-continued

```
            515                 520                 525
Arg Leu Leu Ala Pro Gln Trp Gln Tyr Ser Arg Ala Thr Ala Thr Ile
    530                 535                 540

Asp His Glu Arg Ala Leu Cys Gln Ser
545                 550
```